US012343027B2

(12) United States Patent
Kovarik et al.

(10) Patent No.: US 12,343,027 B2
(45) Date of Patent: *Jul. 1, 2025

(54) MEDICAL INSTRUMENTS FOR PERFORMING A MINIMALLY-INVASIVE PROCEDURE

(71) Applicants: Carter J. Kovarik, Englewood, CO (US); Joseph E. Kovarik, Englewood, CO (US)

(72) Inventors: Carter J. Kovarik, Englewood, CO (US); Joseph E. Kovarik, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/436,427

(22) Filed: Feb. 8, 2024

(65) Prior Publication Data

US 2024/0180573 A1    Jun. 6, 2024

Related U.S. Application Data

(63) Continuation-in-part of application No. 17/396,849, filed on Aug. 9, 2021, now Pat. No. 11,896,252,
(Continued)

(51) Int. Cl.
*A61B 17/221* (2006.01)
*A61B 1/05* (2006.01)
(Continued)

(52) U.S. Cl.
CPC .............. *A61B 17/221* (2013.01); *A61B 1/05* (2013.01); *A61B 1/0684* (2013.01);
(Continued)

(58) Field of Classification Search
CPC . A61B 17/22; A61B 17/221; A61B 17/22031; A61B 17/285; A61B 17/29;
(Continued)

(56) References Cited

U.S. PATENT DOCUMENTS 388,776 A    8/1888    Hal
826,160 A    7/1906    Hall
(Continued)

FOREIGN PATENT DOCUMENTS

FR    1080718    12/1954
WO    WO 2015/038487    3/2015

OTHER PUBLICATIONS

U.S. Appl. No. 29/462,798, filed Aug. 8, 2013, Kovarik et al.
(Continued)

*Primary Examiner* — Vi X Nguyen
(74) *Attorney, Agent, or Firm* — Sheridan Ross P.C.

(57) ABSTRACT

An apparatus for performing a minimally-invasive procedure having a shaft with a flexible portion that extends distally from a handle portion and an actuatable tool head assembly that includes a sharp cutting implement at its other end. The handle portion includes an actuatable trigger operatively connected to a pull member such that actuation of the trigger moves the pull member and selectively positions the actuatable tool head assembly.

9 Claims, 10 Drawing Sheets

Related U.S. Application Data which is a continuation of application No. 16/295,214, filed on Mar. 7, 2019, now Pat. No. 11,083,475, which is a continuation-in-part of application No. 15/431,044, filed on Feb. 13, 2017, now Pat. No. 10,226,266, which is a continuation-in-part of application No. 14/822,238, filed on Aug. 10, 2015, now Pat. No. 9,901,245, which is a continuation-in-part of application No. 14/684,000, filed on Apr. 10, 2015, now Pat. No. 9,592,066, which is a continuation-in-part of application No. 14/539,021, filed on Nov. 12, 2014, now Pat. No. 9,832,980, which is a continuation-in-part of application No. 14/535,539, filed on Nov. 7, 2014, now Pat. No. 9,095,127, which is a continuation-in-part of application No. 14/290,207, filed on May 29, 2014, now Pat. No. 8,985,659, which is a continuation-in-part of application No. 14/163,521, filed on Jan. 24, 2014, now Pat. No. 8,833,817, which is a continuation-in-part of application No. 14/078,830, filed on Nov. 13, 2013, now Pat. No. 8,807,615, which is a continuation-in-part of application No. 13/771,813, filed on Feb. 20, 2013, now Pat. No. 8,585,114.

(60) Provisional application No. 61/601,789, filed on Feb. 22, 2012.

(51) Int. Cl.
| | | |
|---|---|---|
| *A61B 1/06* | (2006.01) | |
| *A61B 17/00* | (2006.01) | |
| *A61B 17/22* | (2006.01) | |
| *A61B 17/32* | (2006.01) | |
| *A61B 17/3201* | (2006.01) | |
| *A61B 90/00* | (2016.01) | |
| *A61B 90/30* | (2016.01) | |

(52) U.S. Cl.
CPC .............. *A61B 2017/00296* (2013.01); *A61B 2017/00323* (2013.01); *A61B 2017/00353* (2013.01); *A61B 2017/00876* (2013.01); *A61B 17/22031* (2013.01); *A61B 2017/22035* (2013.01); *A61B 2017/2215* (2013.01); *A61B 17/320016* (2013.01); *A61B 17/3201* (2013.01); *A61B 90/30* (2016.02); *A61B 90/361* (2016.02); *A61B 2090/3616* (2016.02)

(58) Field of Classification Search
CPC ................ A61B 17/32; A61B 17/3205; A61B 2017/00991; A61B 2017/2212; A61B 2017/2215; A61B 1/06; A61B 1/05
See application file for complete search history.

(56) References Cited

U.S. PATENT DOCUMENTS

| | | |
|---|---|---|
| 944,214 A | 12/1909 | Rydquist |
| 1,051,374 A | 1/1913 | Agin |
| 1,519,938 A | 12/1924 | Smith |
| 1,957,944 A | 5/1934 | Dexter |
| 2,613,100 A | 10/1952 | Casey |
| 2,616,741 A | 11/1952 | Ziese |
| 2,947,564 A | 8/1960 | Winther |
| 3,219,376 A | 11/1965 | Peters |
| 3,266,059 A | 8/1966 | Stelle |
| 3,290,080 A | 12/1966 | Dawson |
| 3,328,066 A | 6/1967 | Johnston |
| 3,346,293 A | 10/1967 | Wilcox |
| 3,527,492 A | 9/1970 | Hollis |
| 3,576,343 A | 4/1971 | Juhlin et al. |
| 3,617,084 A | 11/1971 | Mares |
| 3,761,121 A | 9/1973 | Reid |
| 3,830,538 A | 8/1974 | Moberg |
| 3,901,545 A | 8/1975 | Shott |
| 3,912,316 A | 10/1975 | Veech |
| 3,934,915 A | 1/1976 | Humpa |
| 4,033,618 A | 7/1977 | Lamb |
| 4,039,216 A | 8/1977 | Soos |
| 4,179,145 A | 12/1979 | Shinsako |
| 4,186,955 A | 2/1980 | Campbell |
| 4,225,174 A | 9/1980 | Hennessy et al. |
| 4,248,468 A | 2/1981 | Hastings |
| 4,253,697 A | 3/1981 | Acosta |
| 4,272,116 A | 6/1981 | Tufte, Jr. |
| 4,374,600 A | 2/1983 | van Zelm |
| 4,393,728 A | 7/1983 | Larson et al. |
| 4,398,759 A | 8/1983 | Manola |
| 4,477,111 A | 10/1984 | Crooks |
| 4,483,562 A | 11/1984 | Schoolman |
| 4,501,230 A | 2/1985 | Talo |
| 4,613,179 A | 9/1986 | van Zelm |
| 4,647,094 A | 3/1987 | Bergkvist et al. |
| 4,669,769 A | 6/1987 | Polder, Jr. |
| 4,709,839 A | 12/1987 | Tucker |
| 4,758,035 A | 7/1988 | Shimasaki |
| 4,863,204 A | 9/1989 | Peters |
| 4,865,371 A | 9/1989 | Egberg |
| 4,878,703 A | 11/1989 | Yoshioka |
| 4,962,957 A | 10/1990 | Traber |
| 5,154,465 A | 10/1992 | Pakosh |
| 5,300,086 A | 4/1994 | Gory et al. |
| 5,380,054 A | 1/1995 | Galvis |
| 5,395,033 A | 3/1995 | Byrne et al. |
| 5,454,378 A | 10/1995 | Palmer et al. |
| 5,503,442 A | 4/1996 | Lee |
| 5,540,470 A | 7/1996 | Lu |
| 5,572,913 A | 11/1996 | Nasiell |
| 5,577,785 A | 11/1996 | Traber et al. |
| D376,967 S | 12/1996 | Fuller |
| 5,590,923 A | 1/1997 | Berger et al. |
| 5,601,321 A | 2/1997 | Simon |
| 5,601,322 A | 2/1997 | Forest |
| 5,628,537 A | 5/1997 | Kiemer |
| 5,647,622 A | 7/1997 | Schectman |
| 5,658,296 A | 8/1997 | Bates et al. |
| 5,667,146 A | 9/1997 | Pimentel et al. |
| 5,707,303 A | 1/1998 | Berkowitz et al. |
| 5,766,196 A | 6/1998 | Griffiths |
| 5,776,196 A | 7/1998 | Matsuzaki et al. |
| 5,778,939 A | 7/1998 | Hok-Yin |
| 5,779,646 A | 7/1998 | Koblish |
| 5,797,927 A | 8/1998 | Yoon |
| 5,822,908 A | 10/1998 | Blanchard |
| 5,823,592 A | 10/1998 | Kalidindi |
| 5,857,723 A | 1/1999 | Mathieu et al. |
| 5,895,082 A | 4/1999 | Kaluzny |
| 5,944,728 A | 8/1999 | Bates |
| 6,042,155 A | 3/2000 | Lockwood |
| 6,062,618 A | 5/2000 | Figueroa |
| 6,106,042 A | 8/2000 | McCloy, Jr. |
| 6,148,773 A | 11/2000 | Bogdahn |
| 6,168,603 B1 | 1/2001 | Leslie et al. |
| D439,402 S | 3/2001 | Johnson |
| 6,257,634 B1 | 7/2001 | Wei |
| 6,331,183 B1 | 12/2001 | Suon |
| 6,457,761 B1 | 10/2002 | Benoit |
| 6,491,698 B1 | 12/2002 | Bates et al. |
| 6,506,209 B2 | 1/2003 | Ouchi |
| 6,508,496 B1 | 1/2003 | Huang |
| 6,513,844 B1 | 2/2003 | Hsu |
| 6,520,556 B1 | 2/2003 | Hsu |
| 6,571,479 B1 | 6/2003 | Wu |
| 6,648,261 B2 | 11/2003 | Irving |
| 6,669,254 B2 | 12/2003 | Thom et al. |
| 6,679,893 B1 | 1/2004 | Tran |
| 6,697,893 B2 * | 2/2004 | Hsiao .................. G06F 13/385 379/333 |
| 6,739,637 B2 | 5/2004 | Hsu |
| 6,796,587 B2 | 9/2004 | Tsou |

(56) References Cited

U.S. PATENT DOCUMENTS

| | | |
|---|---|---|
| 6,845,736 B1 | 1/2005 | Anderson |
| 6,848,731 B2 | 2/2005 | Khubani et al. |
| 6,860,668 B2 | 3/2005 | Ibrahim et al. |
| 6,874,833 B2 | 4/2005 | Keith et al. |
| 6,971,695 B2 | 12/2005 | Backstrom |
| 7,004,520 B2 | 2/2006 | Khubani et al. |
| 7,066,411 B2 | 6/2006 | Male et al. |
| 7,093,869 B2 | 8/2006 | Jung |
| 7,147,650 B2 | 12/2006 | Lee |
| 7,169,154 B1 | 1/2007 | Que et al. |
| 7,261,349 B1 | 8/2007 | Gregor |
| 7,281,740 B1 | 10/2007 | Fields |
| 7,325,849 B2 | 2/2008 | Jones |
| 7,338,434 B1 | 3/2008 | Haarstad et al. |
| 7,344,171 B1 | 3/2008 | McMullan |
| 7,371,210 B2 | 5/2008 | Brock et al. |
| 7,448,659 B1 | 11/2008 | Auseklis |
| D591,122 S | 4/2009 | Buzby et al. |
| 7,533,906 B2 * | 5/2009 | Luettgen ................ H01R 35/00 285/146.1 |
| 7,553,314 B2 | 6/2009 | Khachin et al. |
| 7,665,782 B2 | 2/2010 | Buzby et al. |
| 7,677,619 B2 | 3/2010 | Hutchings et al. |
| 7,695,035 B2 | 4/2010 | Sumner et al. |
| 7,708,758 B2 | 5/2010 | Lee et al. |
| 7,744,136 B2 | 6/2010 | Waltz |
| 7,854,738 B2 | 12/2010 | Lee et al. |
| D632,069 S | 2/2011 | Thiessens |
| 7,934,756 B2 | 5/2011 | Kroeze |
| 7,980,609 B2 | 7/2011 | Khubani |
| 7,992,907 B1 | 8/2011 | DeJesus |
| 8,047,236 B2 | 11/2011 | Perry |
| 8,061,751 B2 | 11/2011 | Hatcher |
| 8,091,936 B1 | 1/2012 | Graziano |
| 8,092,489 B2 | 1/2012 | Ewers et al. |
| 8,197,493 B2 | 6/2012 | Ferrera et al. |
| 8,317,820 B2 | 11/2012 | Surti |
| 8,425,408 B2 | 4/2013 | Boulais et al. |
| 8,449,007 B2 | 5/2013 | Farmer |
| 8,453,637 B2 | 6/2013 | Tanaka et al. |
| 8,469,970 B2 | 6/2013 | Diamant et al. |
| 8,480,688 B2 | 7/2013 | Boulnois et al. |
| 8,500,180 B2 | 8/2013 | Buzby et al. |
| 8,528,850 B2 | 9/2013 | Bogdahn |
| 8,529,379 B1 | 9/2013 | Faircloth |
| 8,585,114 B2 | 11/2013 | Kovarik et al. |
| 8,585,712 B2 | 11/2013 | O'Prey et al. |
| 8,602,917 B2 | 12/2013 | Bennett |
| 8,622,992 B2 | 1/2014 | Banet et al. |
| 8,702,731 B2 | 4/2014 | Saliman |
| 8,721,311 B2 | 5/2014 | Thomas et al. |
| 8,721,826 B2 | 5/2014 | Hart et al. |
| 8,747,424 B2 | 6/2014 | Taylor et al. |
| 8,795,325 B2 | 8/2014 | Taylor et al. |
| 8,801,752 B2 | 8/2014 | Fortier et al. |
| 8,807,615 B2 | 8/2014 | Kovarik et al. |
| 8,814,892 B2 | 8/2014 | Galdonik et al. |
| 8,827,134 B2 | 9/2014 | Viola et al. |
| 8,827,948 B2 | 9/2014 | Romo et al. |
| 8,833,817 B2 | 9/2014 | Kovarik et al. |
| 8,893,749 B2 | 11/2014 | Perry |
| 8,911,471 B2 | 12/2014 | Spivey et al. |
| D720,589 S | 1/2015 | Thomas et al. |
| 8,926,598 B2 | 1/2015 | Mollere et al. |
| 8,940,000 B2 | 1/2015 | Kasvikis et al. |
| 8,979,832 B2 | 3/2015 | Asselin et al. |
| 8,985,659 B2 | 3/2015 | Kovarik et al. |
| 9,001,434 B2 | 4/2015 | Chen et al. |
| 9,005,144 B2 | 4/2015 | Slayton et al. |
| 9,078,682 B2 | 7/2015 | Lenker et al. |
| 9,095,127 B2 | 8/2015 | Kovarik et al. |
| 9,101,358 B2 | 8/2015 | Kerr et al. |
| 9,138,132 B2 | 9/2015 | Belson |
| 9,198,561 B2 | 12/2015 | Smith et al. |
| 9,226,751 B2 | 1/2016 | Shelton, IV et al. |
| 9,492,167 B2 | 11/2016 | Shelton, IV et al. |
| 9,492,189 B2 | 11/2016 | Williams et al. |
| 9,832,980 B2 * | 12/2017 | Kovarik .................... B25J 1/02 |
| 9,901,245 B2 * | 2/2018 | Kovarik ............... A61B 1/0676 |
| 9,902,245 B2 | 2/2018 | Kovarik |
| 11,083,475 B2 * | 8/2021 | Kovarik ............... A61B 1/0684 |
| 11,896,252 B2 | 2/2024 | Kovarik |
| 2003/0236549 A1 | 12/2003 | Bonadio et al. |
| 2004/0039406 A1 * | 2/2004 | Jessen ................ A61B 17/3496 606/167 |
| 2004/0236316 A1 | 11/2004 | Danitz et al. |
| 2005/0057055 A1 | 3/2005 | Deal |
| 2005/0103903 A1 | 5/2005 | Shamir et al. |
| 2005/0131279 A1 | 6/2005 | Boulais et al. |
| 2005/0273085 A1 | 12/2005 | Hinman et al. |
| 2006/0178560 A1 | 8/2006 | Saadat |
| 2006/0206101 A1 | 9/2006 | Lee |
| 2006/0221598 A1 | 10/2006 | March et al. |
| 2007/0085358 A1 | 4/2007 | Robinson et al. |
| 2007/0276430 A1 | 11/2007 | Lee et al. |
| 2008/0115400 A1 | 5/2008 | Capio |
| 2009/0200812 A1 | 8/2009 | Mambru |
| 2010/0021279 A1 | 1/2010 | Buzby et al. |
| 2010/0204711 A1 | 8/2010 | Kear et al. |
| 2010/0286709 A1 | 11/2010 | Diamant et al. |
| 2010/0312338 A1 | 12/2010 | Gonzales et al. |
| 2011/0184459 A1 | 7/2011 | Malkowski et al. |
| 2011/0196414 A1 | 8/2011 | Porter et al. |
| 2011/0217482 A1 | 9/2011 | Thomas et al. |
| 2012/0060878 A1 | 3/2012 | Thiessens |
| 2013/0096457 A1 | 4/2013 | Qiu et al. |
| 2013/0158592 A1 | 6/2013 | Porter |
| 2013/0317516 A1 | 11/2013 | Teague et al. |
| 2014/0047757 A1 | 2/2014 | Miller et al. |
| 2014/0054912 A1 | 2/2014 | Bustos |
| 2014/0121672 A1 | 5/2014 | Folk |
| 2014/0152031 A1 | 6/2014 | Ballacchino |
| 2014/0155862 A1 | 6/2014 | Baxter et al. |
| 2014/0155908 A1 | 6/2014 | Rosenbluth et al. |
| 2014/0257245 A1 | 9/2014 | Rosenbluth et al. |
| 2014/0275950 A1 | 9/2014 | Hoseit |
| 2014/0276920 A1 | 9/2014 | Hendrick et al. |
| 2014/0277015 A1 | 9/2014 | Stinis |
| 2014/0309657 A1 | 10/2014 | Ben-Ami |
| 2014/0358162 A1 | 12/2014 | Valdastri et al. |
| 2015/0052798 A1 | 2/2015 | Kovarik et al. |
| 2015/0080937 A1 | 3/2015 | Davidson |
| 2015/0088122 A1 | 3/2015 | Jensen |
| 2015/0164522 A1 | 6/2015 | Budiman et al. |
| 2015/0230811 A1 | 8/2015 | Kovarik et al. |
| 2016/0030596 A1 | 2/2016 | Kheir et al. |
| 2016/0109046 A1 | 4/2016 | Lee et al. |
| 2016/0134068 A1 | 5/2016 | De Jong et al. |
| 2016/0228187 A1 | 8/2016 | Gross |
| 2016/0262763 A1 | 9/2016 | Shankarsetty et al. |

OTHER PUBLICATIONS

U.S. Appl. No. 29/558,227, filed Mar. 16, 2016, Kovarik et al.
U.S. Appl. No. 10/226,266, filed Mar. 12, 2019, Kovarik et al.
"Robot Claw Grabber" Toysmith, 2005, retrieved from: http://web.archive.org/web/20050227054600/http://www.toys2wish4.com/robclawgrab.ht,ml, retrieved on Aug. 16, 2013, 3 pages.
Seppa, "Snagging clots upgrades stroke care," Science News, 2015, 2 pages.
International Search Report and Written Opinion for International (PCT) Patent Application No. PCT/US2013/054275 mailed Jan. 10, 2014, 10 pages.
International Preliminary Report on Patentability for International (PCT) Patent Application No. PCT/US2013/054275 mailed Sep. 3, 2015, 9 pages.
Official Action for U.S. Appl. No. 13/771,813 mailed Jun. 14, 2013, 9 pages.
Official Action for U.S. Appl. No. 13/771,813 mailed Sep. 5, 2013, 9 pages.
Notice of Allowance for U.S. Appl. No. 13/771,813 mailed Sep. 20, 2013, 6 pages.

(56) References Cited

OTHER PUBLICATIONS

Official Action for U.S. Appl. No. 14/078,830 mailed Mar. 17, 2014, 7 pages.
Notice of Allowance for U.S. Appl. No. 14/078,830 mailed Apr. 11, 2014, 5 pages.
Official Action for U.S. Appl. No. 14/290,207, mailed Oct. 27, 2014, 8 pages.
Notice of Allowance for U.S. Appl. No. 14/290,207, mailed Nov. 19, 2014, 7 pages.
Notice of Allowance for U.S. Appl. No. 14/535,539, mailed Apr. 1, 2015, 6 pages.
Official Action for U.S. Appl. No. 14/684,000, mailed Aug. 17, 2016, 13 pages.
Official Action for U.S. Appl. No. 29/462,798, mailed Jul. 17, 2015, 8 pages.
Advisory Action for U.S. Appl. No. 29/462,798, mailed Feb. 25, 2016, 5 pages.
Final Action for U.S. Appl. No. 29/462,798, mailed Oct. 28, 2015, 6 pages.
Official Action for U.S. Appl. No. 14/539,021, mailed Oct. 28, 2016, 16 pages.
Notice of Allowance for U.S. Appl. No. 14/684,000, mailed Nov. 15, 2016, 7 pages.
Official Action for U.S. Appl. No. 29/558,227, mailed Sep. 26, 2016, 7 pages.
Notice of Allowance for U.S. Appl. No. 29/558,227, mailed Oct. 25, 2016, 6 pages.

\* cited by examiner

MEDICAL INSTRUMENTS FOR PERFORMING A MINIMALLY-INVASIVE PROCEDURE

RELATED APPLICATIONS

This application is a continuation-in-part of U.S. patent application Ser. No. 17/396,849, filed Aug. 9, 2021 (now U.S. Pat. No. 11,896,252, issued Feb. 13, 2024), which is a continuation of U.S. patent application Ser. No. 16/295,214, filed on Mar. 7, 2019 (now U.S. Pat. No. 11,083,475, issued Aug. 10, 2021), which is a continuation-in-part application of U.S. patent application Ser. No. 15/431,044, filed on Feb. 13, 2017 (now U.S. Pat. No. 10,226,266, issued Mar. 12, 2019), which is a continuation-in-part of U.S. patent application Ser. No. 14/822,238, filed on Aug. 10, 2015 (now U.S. Pat. No. 9,901,245, issued Feb. 27, 2018), which is a continuation-in-part application of U.S. patent application Ser. No. 14/684,000, filed on Apr. 10, 2015 (now U.S. Pat. No. 9,592,066, issued Mar. 14, 2017), which is a continuation-in-part application of Ser. No. 14/539,021, filed on Nov. 12, 2014 (now U.S. Pat. No. 9,832,980, issued Dec. 5, 2017), which is a continuation-in-part of U.S. patent application Ser. No. 14/535,539, filed on Nov. 7, 2014 (now issued U.S. Pat. No. 9,095,127, issued Aug. 4, 2015), which is a continuation-in-part of U.S. patent application Ser. No. 14/290,207, filed on May 29, 2014 (now issued U.S. Pat. No. 8,985,659, issued Mar. 24, 2015, which is a continuation-in-part of U.S. patent application Ser. No. 14/163,521 filed on Jan. 24, 2014 (now U.S. Pat. No. 8,833,817, issued Sep. 16, 2014), which is a continuation-in-part application of U.S. patent application Ser. No. 14/078,830 filed on Nov. 13, 2013 (now U.S. Pat. No. 8,807,615, issued Aug. 19, 2014), which is a continuation-in-part of U.S. patent application Ser. No. 13/771,813 filed on Feb. 20, 2013 (now U.S. Pat. No. 8,585,114, issued Nov. 19, 2013), and claims priority from U.S. Provisional Patent Application Ser. No. 61/601,789, filed on Feb. 22, 2012. The entire disclosure of the prior applications are considered to be part of the disclosure of the accompanying application and are hereby incorporated by reference.

FIELD OF THE INVENTION

The present invention is directed to a selectively bendable remote access gripping tool that includes a jaw portion having a pair of jaws or nets movable relative to each other between clamped and opened positions thereof, a handle portion spaced apart from the jaw portion by a bendable central portion that has a hollow, corrugated member that is bendable, a cord extending through the central portion of the hollow bendable member that connects the jaw portion and the handle portion.

BACKGROUND OF THE INVENTION

In the fields of surgery, dentistry and orthodontia, professionals often have a desire to reach interior portions of a person's anatomy to grasp objects, tissue, etc. Many prior art devices to achieve such objectives are linear with grasping jaws, while still others have a flexible portion that facilitates some angular adjustments. Such tools, however, are often complicated in terms of construction, often employing rails and jointed connections that rotate relative to each other to facilitate desired flexibility of the tool along at least an extent thereof. A simpler, cost effective, and versatile tool is therefore desired that can facilitate such professional's procedures involving reaching into interior portions of a person's anatomy to grasp objects, tissue, etc.

Occluded blood vessels can be caused by a blood clot (i.e. thrombus) that forms in the blood vessel or by a blood clot that travels downstream (i.e. embolus). The blockage disrupts blood flow, which prevents oxygen and nutrients from being delivered to their intended locations. Tissue distal of a blood clot that is deprived of oxygen and nutrients can no longer function properly. For every minute that treatment is delayed, additional cellular death of critical tissue can occur.

Current technology for blood flow restoration, for example for treating cerebral arteries occluded by thrombi, can often take hours to reestablish flow in the artery, and can lead to unintended complications. Apparatuses and methods for treating cerebral thrombi are often ineffective or only partially effective at resolving thrombus removal, and may result in distal embolization or embolization of uninvolved arteries. For example, some current devices are designed to pierce through a thrombus, or are designed to deploy completely distal of the thrombus before engaging the thrombus. These devices can often fail to capture all of a thrombus, can damage vessel walls distal of a thrombus, can be difficult to maneuver, can unintentionally dislodge portions of a thrombus prior to capture, and/or can take significant amounts of time to restore blood flow. Acute stroke is one of the leading causes of death worldwide; an estimated 85% of acute strokes are caused by cerebral ischemia. About 30% to 40% are large-vessel occlusions amenable to intervention.

A stroke is caused by a rupture or an occlusion of a blood vessel which leads to oxygen deprivation in the brain. In the United States, nearly eight hundred thousand people suffer a stroke each year, and over one hundred and forty thousand people die from strokes each year. Stroke is the leading cause of serious, long-term disability in the United States and the third leading cause of death. Approximately three-quarters of strokes in the United States are first attacks and approximately one-quarter are recurrent attacks. Eighty seven percent are ischemic in nature, meaning that they are caused by a restriction, obstruction, or blockage in the blood supply of the patient, and thirteen percent are hemorrhagic, meaning that they are caused by excessive bleeding. The economic cost of stroke to the United States is over forty billion dollars per year. The direct costs of medical care and therapy are almost thirty billion dollars per year.

It is well known in the art that the extent to which treatment of a stroke is successful in preventing death and/or in reducing the consequent damage to a patient is largely influenced by the time which elapses between the onset of the stroke and the proper treatment of the stroke. The elapsed time is a function of not only whether or not a patient is able to get to a medical facility or hospital, but also the nature of the stroke and whether or not the particular medical facility or hospital to which the patient is initially brought is best equipped to treat the stroke. The capability of the medical facility to treat the particular stroke may not be known until the patient is properly evaluated and analyzed.

Blood clots or emboli to the pulmonary arteries of the lung, the brain, the peripheral arteries of the extremities, in the venous system, or in dialysis access vessels are potentially life and/or limb threatening conditions. Delivered systemically, thrombolytic drugs typically require several hours to days to accomplish dissolving these clots. In cases where time is of the essence, such as cases where an arterial thromboembolism is causing severe tissue ischemia (e.g., an evolving stroke or an evolving myocardial infarction) the time which may be required for the thrombolytic drugs to fully lyse or dissolve the blood clot and restore arterial blood flow may be too long to avoid or minimize the impending infarction. Thrombolytic drugs also have an approximately 5% incidence of major complications such as hemorrhage and stroke. Conventional devices are often difficult to advance into curved and tortuous vessels such as the pulmonary arteries. While devices available in the marketplace may break up a clot and suction the resulting particles out, they often infuse large volumes of fluid as part of their action, which may be physiologically difficult to handle for the patient.

There is a great need for improved devices, device systems, and methods for increasing blood flow through a blood vessel as described herein. None of the existing medical mechanical thrombectomy devices address all necessary needs to date. The high prevalence and high rates of death and disability caused by ischemic stroke call for the urgent need for more effective and accessible therapeutic alternatives to the population at risk.

There is therefore a need for devices that can rapidly and safely be used during intravascular interventions to prevent distal embolization by capture of blood clots or atheromatous material.

Transluminal, catheter-based interventional procedures are highly operator-skill-dependent, and can be difficult or impossible to perform in small or tortuous blood vessels. None of the transluminally deployable clot capturing type of catheters are perfectly designed to address ischemic strokes because, while they are typically capable of removing an offending blood clot without the need for suction or application of energy (e.g., laser, ultrasound) which could be injurious to the delicate, small blood vessels of the brain, they are a) not equipped with appropriate guidewire passage lumens to allow them to be passed over previously inserted, small-diameter (e.g., 0.006-0.018 inch) guidewires, b) they are not adapted for rapid exchange over a guidewire of standard length (e.g., a guidewire which is less than twice the length of the catheter) and c) the clot capturing receptacles of these catheters are not optimally constructed and configured for removal of clots from very small blood vessels as are typically found in the brain.

Major disadvantages of existing mechanical thrombectomy devices include that they often can only capture and remove embolus that are firm and can be held together as one piece and are not capable of capturing small emboli that break off from a larger embolus, and can lead to complications such as blockage of distal smaller vessels, vessel dissection, perforation and hemorrhage arise as a result of over-manipulation in the vessel.

Moreover, some existing devices may capture an embolus, but then lose grasp of it so that it migrates and deposits it incidentally in another area of the neurovasculature, creating the potential for a new stroke in a different part of the neurovasculature. Existing mechanical thrombectomy devices are also constructed of two or more distinct pieces that require either joints or bonding between a delivery system and a treatment device, with this connection presenting occasions of unintentional separation of the two pieces, thus leaving the treatment device in the body during embolus retrieval. Also, the treatment portion of conventional mechanical thrombectomy devices tend to be larger than the delivery system.

Guide wires stiff enough to penetrate hard occlusions have the disadvantage that their inflexibility and straight tips make navigating through tortuous vessels difficult and increase the risk of vessel perforation.

Conventional therapies to treat stroke include thrombolytic therapy and catheter directed thrombectomy (CDT). Drawbacks of thrombolytic therapy include hemorrhagic risk. Conventional CDT systems often employ an introducer sheath or catheter to the target site, with such larger introducer sheaths increasing the risk of trauma to the patient, and being harder to navigate through the vessels.

Conventional catheter devices use a shaft comprising an outer tube connected to the sheath and an inner shaft such that the proximal movement of the sheath is accomplished by imposing an endwise tension on the outer tube, with the inner shaft carrying an endwise compression stress. Such a catheter effectively has telescoping inner and outer tubes, with a deployable wire nest being radially constrained by the outer tube. Retraction of the outer tube removes the constraint on the clot removal device and permits it to expand to its deployed configuration. One disadvantage is that in use, such devices require the medical practitioner to maintain the device in an unchanged axial disposition relative to the site in the body of the patient, while pulling back on the outer tube of the shaft to release the expandable portion of the device. This pulling back of the outer tube requires relative movement of the outer tube in the bodily lumen (or guide catheter) in which it has been advanced to the site of the thrombus. Any friction or resistance to axial movement of the outer tube in the lumen in which it is located hinders the objective of maintaining the device in a precise disposition.

One conventional device is the Merci retrieval device made by Concentric Medical, and another is sold by Penumbra, Inc., which employs suction to pull out a clot. Both of these devices are often unsuccessful in their intended functions. Recent reports indicate that the Trevo and Solataire devices, also of similar operation in terms of employing outer and inner luminal movements, are superior in various respects to the Merci and Penumbra devices. All of these devices, however, rely upon a dual lumen translational construction to achieve employment of a thrombus capture device. The present invention addresses this issue by providing a distinctly different and better way to achieve the objective of safely, promptly and effectively capturing a thrombus and reducing its volume while being conveyed out of the body.

Existing common concerns of physicians who practice angioplasty include: concern that the thrombectomy device may capture an embolus, only to lose hold of it and accidentally deposit it in another area of the neurovasculature; concern that the device may not be able to capture a 'break-off' piece of the embolus, which may migrate further into the neurovasculature; concern that the relatively large device may prevent it from accessing and treating clots in small-diameter vessels; and concern that the devices usually require adhesive joining or bonding between the delivery system and the treatment device. In the latter case, in some instances a concern is that the adhesive bonding may fail, presenting the possibility that the pieces may separate, presenting a serious complication in the procedure. These concerns are addressed by the present invention as the pair of netting structures ensures secure capturing of a thrombus without the threat that there would be any break off pieces of the emboli. The small profile provided by the present embodiments of the present invention provides for a way to access even narrow, convoluted blood vessels and to capture an emboli in a straightforward netting operation with the operation of a haptic friendly trigger operation of a handle by a surgeon.

A large number of medical procedures require the use of a medical device to remove an obstruction from a body lumen, vessel, or other organ. An inherent risk in such procedures is that mobilizing or otherwise disturbing the obstruction can potentially create further harm if the obstruction or a fragment thereof dislodges from the retrieval device. If a particle or the obstruction breaks free from the device and flows downstream, it is highly likely that the particle or obstruction will become trapped in smaller and more tortuous anatomy. In many cases, the physician will no longer be able to use the same retrieval device to again remove the obstruction because the size of the device may prevent advancing the device to the site of the new obstruction. Such concerns are addressed by the present invention as the netting structure of preferred embodiments captures the entire thrombus and thus avoids the threats associated with breaking up of the thrombus as is a common concern with conventional devices.

A variety of mechanisms have been employed to steer conventional catheters, with some specialized catheter systems having dozens of pull wires being articulated by a dedicated motor attached to the proximal end. Alternative articulation systems utilize electrically actuated shape memory alloy structures, piezoelectric actuation, phase change actuation, and the like. These steerable systems increase the complexity and price of devices and have questionable benefits in practice. As articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. The result is that existing devices are deficient in various respects, hampering the ability of a surgeon to promptly advance a tool through a blood vessel to the site of a thrombus, and to then effectively capture the entire thrombus/emboli in a manner that does not pose a risk that pieces of the thrombus/emboli will dislodge and potentially cause other problems. Existing devices further do not permit the thrombus to be reduced inside a secure capturing confine so that damage to the vessels is avoided when attempting to remove the thrombus from the blood vessels.

In still other procedures that do not involve a thrombus in brain tissue, for example, the treatment of deep vein thrombosis (DVT), which results from a clot that forms in one of the large veins of the leg leading to venous hypertension and inflammation, a need exists for a better system and method to remove occlusions. Venous thrombosis can occur in healthy as well as sick individuals. A complication most commonly associated with venous thrombosis is the condition known as "pulmonary embolism." A pulmonary embolus is actually a clot that has broken free from a vein wall and has traveled to the pulmonary artery, and then, if not removed, to a lung. When an embolus blocks a blood vessel in the lung, breathing is compromised and death may ensue. Accordingly, early treatment of DVT is desirable.

The longer the occlusion remains, the more risk of damaging the valves of the vein that normally stop blood from flowing backwards. A confluence of symptoms comprised of chronic pain, swelling, skin ulcerations and pain can develop that can markedly reduce the quality of life. A rapid, direct method to remove clots in the leg, with minimal lytic drugs, is needed to treat DVT patients. Such a device and method is provided by the present invention.

Over the last 10 years there has been major technological breakthrough for the mechanical thrombectomy devices, starting with MERCI® retriever and reaching stent retriever devices (e.g. SOLITAIRE® and TREVOR). As compared to such devices, however, the present invention provides a device and related method to provide a more flexible profile, allowing easier navigation and faster access to vascular occlusion site. The importance of agility in the endovascular treatment in order to prevent irreversible damage to a person's brain is immense and the provision of a device that is simple, easily employed and that can be used well within the 3-hour time period after a stroke to save the person's life and brain is a central focus of the present invention.

SUMMARY OF THE INVENTION

Recent developments in medical technology and associated treatments have been focused on clearing or removing thromboembolisms or "blood clots" from the cervical and cerebral vasculature in order to treat thromboembolic stroke victims. Thromboembolic stroke is a life threatening condition that consists of arrested blood flow to a region of the brain due to a thromboembolisum blocking a blood vessel feeding that region. Such thrombi often originate in the left heart chambers, break free into the aorta and flow downstream into the cervical neck arteries e.g. carotid arteries, and then ultimately lodge into a narrowed vessel somewhere down the narrowing vascular tree of the cerebral arteries associated with the brain in the head. Once lodged, the thrombus occludes flow along the vessel downstream of the blockage, thus arresting blood flow to the downstream blood vessel and causing the stroke.

Occlusion of a blood vessel can be caused by a thrombus (i.e., blood clot) that forms in a blood vessel, or by an embolus, i.e., a blood clot that travels downstream. The blockage disrupts blood flow, which prevents oxygen and nutrients from being delivered to their intended locations. Tissue distal to a blood clot that is deprived of oxygen and nutrients can no longer function properly. For every minute that treatment is delayed, additional cellular death of critical tissue can occur. As used herein a "vessel" or "lumen" refers to blood vessels (including arteries and veins) and other suitable body organs having a lumen, such as the gastrointestinal tract (e.g., esophagus, stomach, small intestine, colon, rectum), bile ducts, urinary bladder, ureter, urethra, trachea, bronchi, and the like. Pulmonary embolisms occur in the pulmonary arteries. Typically, access to such pulmonary embolisms is achieved using an introducer device that is inserted into a patient into their femoral vein in the pelvic area of the patient. The tools and devices needed to treat the pulmonary embolism are then inserted through the introducer into the femoral vein through the inferior vena cava to the patient's heart. Other access locations into the venous circulatory system of a patient are possible, for example, the user can gain access through the jugular vein, the subclavian vein, the brachial vein or any other vein that connects or eventually leads to the superior vena cava. Use of other vessels that are closer to right atrium of the patient's heart are attractive because it reduces the length of the instruments needed to reach the pulmonary embolism.

Current technology for blood flow restoration, for example for treating cerebral arteries occluded by thrombi, can often take hours to reestablish flow in the artery, and can lead to unintended complications. Apparatus and methods for treating cerebral thrombi are often ineffective or only partially effective at resolving thrombus removal, and may result in distal embolization or embolization of uninvolved arteries. For example, some current devices are designed to pierce through a thrombus, or are designed to deploy distally to the thrombus before engaging the thrombus. These devices often fail to capture all of a thrombus, can damage vessel walls distal of a thrombus, can be difficult to maneuver, can unintentionally dislodge portions of a thrombus prior to capture, and/or can take significant amounts of time to restore blood flow. Dislodgment of portions of the thrombus, referred to as secondary emboli, often cause complications because the secondary emboli may travel downstream and occlude other vessels or arteries.

Various embodiments of the present invention are directed to "basket" retrieval surgical devices that have a net assembly, such as a pair of nets, at a distal end able to surround a captured stone, thrombus or calculi during retrieval. Unlike prior art devices, which while having basket-type devices, collapse into the distal end of a catheter during insertion, and are then extended from the end of the catheter when deployed, preferred embodiments of the present invention do not require retraction of the net assemblies into a catheter. Some types of these instruments employ a retrieval collapsible basket arranged within a flexible catheter formed as a tubular sheath with the basket and the sheath moving relative to each other to open and close the basket. The basket can retract inside the sheath or protract from the catheter to open the basket to form a cage to thus allow entrance of the object into the basket. Retraction of the basket into the sheath results in the cage collapsing and entrapping the object in the basket. Other types of retrieval devices employ miniaturized grasping legs that are unattached at a distal end of the grabber and joined at a proximal base of the grabber. The legs are movable relative to the sheath to achieve a contracted position within the sheath and an extended position outside of the sheath in the form of an open grasper. The distal ends of the legs are farther apart from each other when the grabber is in the open position than when in the closed position. The grasping legs are typically formed of elastic wires with insufficient rigidity to reliably hold retrieved objects and thus, the legs may deform and drop the objects during operation.

Other traditional devices employ a single loop snare that requires skilled manipulation to capture a desired object. In an attempt to provide a snare with improved cross sectional vessel coverage, multi loop snares have been developed. These snares include loops which are joined only at their proximal ends to a manipulation shaft, and otherwise are not joined at any point between the shaft and the distal ends of the loops. Such loops often become displaced and/or entangled, thus preventing the snare from opening during operation Moreover, unlike prior art basket-type retrieval devices, which typically require a physician to advance the device past a stone mass, followed by deployment of the retrieval device, and subsequent pulling back of the basket toward the stone to capture the stone, various preferred embodiments of the present invention provide the ability to secure stone masses without having to move the device past a stone.

Additionally, prior art basket retrieval devices often become stuck or wedged during stone removal, resulting in damage to surrounding tissue or tissue lining caused by a physician forcing the basket and stone through an area in which the stone has become stuck or wedged. To avoid such damage, it may be necessary to release the stone and break it into smaller fragments. Unfortunately, typical basket retrieval devices do not allow the physician to release easily the stone and continue breaking it up before removal is again attempted. Similar situations arise using prior art surgical "graspers" instead of a basket device. Typical graspers employ three or four prongs that are manipulated to capture a stone from the front side of the stone, by grasping it. When a stone becomes stuck or wedged during removal, such graspers are able to release the stone. Unfortunately, typical graspers often do not hold on to stones as well as baskets. Moreover, it can be difficult to capture a stone using a grasper, and once captured, it is easy for the stone to be released inadvertently. Thus, in the past, over the course of a procedure, a physician often needs to use both graspers and basket-type devices to manipulate a stone, break up the stone, and remove fragments of the stone. Using current graspers and baskets, a physician may need to switch devices during the procedure. Switching devices typically requires withdrawal of one device and insertion of another. In contrast, certain embodiments of the present invention employ cutting jaws that can be employed once the pair of nets captures the thrombi so as to reduce the size of the mass and make it easier to remove form the body.

Certain embodiments of the surgical device include an assembly having a plurality of spring-like finger members, which may be composed of nitinol, stainless steel, a Co—Cr alloy, or a titanium alloy, though other materials also may be used. In various aspects of the present invention, a surgical retrieval device is inserted into a body tract while the multi-fingered retrieval assembly is in a closed position as the retrieval device is placed in a vessel and then maneuvered to capture material. Once the material is captured, the retrieval device, along with the material, are withdrawn from the body. In various embodiments, netting material can be associated with the plurality of fingers so as to achieve the advantages of both grasper and the basket-type devices. Thus, a surgical retrieval device may be adapted to have a distal end (preferably replaceable) that permits the device to be used as a grasper for grasping material similar to forceps. In other situations, the distal end can be a multi-fingered retrieval net assembly so that the device may be used as a basket-type retrieval device to capture material within a basket formed by the netting stretched between the fingers of the multi-finger retrieval assembly. In preferred embodiments, the distal portion of the preferred surgical retrieval device of the present invention is designed to capture not only the thrombus, but also any secondary emboli, and therefore, prevent secondary emboli from traveling downstream during clot retrieval.

There has been a long felt an unmet need to provide a surgical device that is adept at removing harder material, such as calcium (e.g. harder than thrombus and plaque). Cutting and removal of such harder materials has generally required additional procedure time and increased risks. The present invention provides such a device as it can capture the thrombus and then employ sharp cutting implements to reduce the size of the same without risk that pieces of the thrombus would escape. It is also important to have a device that is easy to use by a physician and is compatible with present therapeutic devices and methods. Embodiments of the present disclosure contemplate various mechanical cutting features provided in combination with the jaws that are compatible with existing protocols.

The present device can reduce the invasiveness and potential trauma previously associated with various medical procedures. The removal of a calculus, such as, for example, a kidney stone, a ureteral stone, a urethral stone, a urinary bladder stone, or a stone in the biliary tree such as a gallbladder stone or a bile duct stone and the like from the body, is one area where the present invention may be used with success. The present device permits the removal of stones and other material from the body without the need for major surgery. Generally, the device is guided through the body to the site of the stone and is used to grasp/net and/or cut up and remove the stone, preferably under the guidance of an endoscope.

One problem with known baskets is that it often is difficult to remove the basket containing the material from the body without damaging the surrounding tissue and it is not possible to release the captured material from the basket. In some instances, a stone is of such a size that it is incapable of being removed while it is captured within the basket. In other instances, the body duct or orifice, such as the ureter or ureteral orifice junction (where the ureter and bladder join), is too small to allow for passage of the basket with the captured stone. If an excessive force is used to attempt to remove the basket and the captured material, tissue may be damaged. Sometimes surgery is required to dislodge both the basket and the captured material. This problem is solved by use of the present invention as its cutting implements can be employed after the stone is captured by the grasping portion/nets, so that its size is reduced so it can be removed without further harming the patient.

Various embodiments of the present invention provide a surgical extractor which is capable of capturing and releasing foreign or biological material (e.g. stones, calculi, etc.), and preferably reduce the size of the captured material so as to make its passage out of the body less harmful to the patient. In accordance with various embodiments of the present invention, a surgical retrieval device, and related methods, use a basket/pair of nets formed by a plurality of legs to retrieve foreign or biological material.

Thus, the selectively bendable remote grasping device of the present invention finds various uses and application in endoscopic surgery. Endoscopic instruments are often preferred over traditional open surgical devices since the use of a natural orifice tends to reduce the post-operative recovery time and complications. Thus, precise placement of a working end of a tool at a desired surgical site through a natural orifice is achievable by use of the present invention, which can engage and/or treat tissue in a number of ways to achieve a diagnostic or therapeutic effect. Prior art devices generally rely upon a moving sheath arrangement where movement of grasping devices at a distal end are controlled through the shaft via longitudinal translations, which can interfere with the flexibility of the shaft. Traditional devices also typically require a significant amount of force necessary to articulate and/or actuate the working end and some surgeons cannot handle such force repeatedly or well. While use of electrical motors have been attempted, surgeons typically prefer to experience feedback from the working end to assure proper operation of the end effector. In contrast to the user-feedback effects that are not suitably realizable in motor-driven devices, the present device provides for a superior haptic feel by a surgeon so that he/she can manipulate the working end of the device to achieve extraction of a stone, thrombus, etc.

Various embodiments of the present invention are directed to the removal of an intravascular or intracavitary thrombus or other material which may frequently require removal to restore blood flow or other normal functionality of an organ system affected.

Various embodiments employ a procedure that involves access to the femoral artery in a patient's leg or the radial artery in the arm, to advance a guidewire/device through the vascular system to the occluded site.

In certain embodiments, the device is guided to intended places in the patient's body by applying magnetic attraction, including for example, existing large magnetic fields using coils outside the patient's body to direct the device distal end inside the heart or brain or other body part of a patient. Thus, the employment of a magnet on the grasping end of the device facilitates such magnetic guidance to a point where a thrombus or stone may be located, thus assisting the travels through convoluted blood vessels, etc.

Access guidewires are known medical devices used in the vasculature or other anatomical passageway to act as a guide for other devices, e.g., a catheter. Typically, the guidewire is inserted into an artery or vein and guided through the vasculature under fluoroscopy (real time x-ray imaging) to the location of interest. While guidewires can be used in combination with the present device, oftentimes this is unnecessary given the ability of the device to be pushed through vessels and then activated to grasp objects therein. The corrugated design of the present invention permits such a pushing of the central column in a manner that permits requisite flexibility to address sharp turns of vascular passages.

Thus, while some have stated that advancing a flexible guidewire and/or catheter through a tortuously branched network of body lumens might be compared to "pushing a rope," in preferred embodiments of the present invention, the articulated corrugated construction of the present invention permits a surgeon to advance the tool as described herein through convoluted blood vessels to reach an occluding thrombus. In preferred embodiments, due to the single aperture in the center of the preferred articulated loc-line-like individual but joined pieces creating a single channel, with a pulling member (cord) passing through the central aperture of the stacked pieces and that connects the distal end with the thrombus capturing end to the handle and trigger end of the device, a surgeon is provided with a device that can traverse the sharp turns of blood vessels. The ability to effectively push the connected articulated pieces so that the pair of nets advance to the position of the thrombus is rendered possible, including when a guidewire (and preferably one that is a fiber optic construction) is first advanced through the blood vessel to the thrombus. In some embodiments, the corrugated device of the present invention is then associated with the guidewire so that the device can be pushed along with the guidewire (e.g. through the central column) to the thrombus. When the pair of nets is pushed along the guidewire to the point of the thrombus, the nets can then be positioned so that they surround the thrombus and then the trigger can be operated to clamp the nets around the thrombus and encompass most if not all of the thrombus. Once the thrombus is entrapped by the pair of nets it can be withdrawn from the blood vessel by pulling it out along with or subsequent to the guidewire being removed. In certain embodiments, the provision of cutting implements permits the thrombus to be reduced in size while inside the enclosed nets. This provides for a way to reduce the volume and size of the thrombus so as to permit easier passage of the thrombus through the convoluted return path through the vasculature.

Still other embodiments employ an encapsulated amount of tPA or another clot dissolving compound such that after the thrombus is captured within the netting assembly as described herein, the fracturing of such encapsulated structure will release the contents of the encapsulated structure so that the captured thrombus can be dissolved, thus reducing its volume or structure such that it is easier to move the thrombus in existing the blood vessels.

In certain preferred embodiments, the central column of the device comprises a corrugated segment comprising a plurality of interconnected connectors, such as "loc-line" plastic elements. For certain embodiments that include the use of particular linked plastic components that comprise the flexible portion of the device, incorporated entirely by this reference are U.S. Pat. No. 6,042,155 to Lockwood; U.S. Pat. No. 5,778,939 to Hok-Yin; U.S. Pat. No. 5,667,146 to Pimental et al.; and U.S. Pat. No. 7,533,906 to Luettgen.

Another aspect of the present invention is directed to effectively sealing the material inside a bag after collection. While methods employing adhesives is preferred, others can also be used, such as with ties, twisting of the bag, spinning the bag after it is filled with material, etc.

Given the flexible nature of the device, it is possible to twist two separate extensions around each other, thus forming a single extension that comprises a twisted (helical) portion of a device, which can have two separate triggers to operate the pulling of cords extending in the separate extended, twisted portions. This facilitates further options for a user in certain situations where an additional set of operable distal features, such as a separate set of jaws, may be useful.

A further object of the present invention is to provide a light source associated with the central portion section in connection with elongate gripper tools. A lighting source can also be positioned at the distal end of the device so that a user can more readily see the distal end and facilitate proper positioning of the distal end to perform operations, such as clamping of jaws around a distant object that may be in a darkened environment. LED lighting sources with small, battery powered energy sources are preferred, but one of skill in the art will appreciate, given the guidance provided herein, the vast variety of other lighting arrangements and features that can be employed while still being within the scope of the claimed invention. A magnifying viewing device (e.g., a distally positioned camera) can also be provided to assist the user in viewing the distal end of the device in particular applications, such as when a detailed and sensitive manipulation of a remote object is required and the user requires magnification of the distal end to properly position the device to perform desired functions.

Various embodiments of the present invention are directed to the removal of intravascular or intracavitary thrombus or other material which may frequently require removal to restore blood flow or other normal functionality of an organ system affected. Various embodiments employ a procedure that involves access to the femoral artery in a patient's leg or the radial artery in the arm, to advance a guidewire/device through the vascular system to the occluded site.

Capturing thrombus material in an enclosure such that it can be removed from the body, without the additional risk that there will be break-away pieces that could present other obstructions, is one advantage of several of the embodiments of the present invention.

In yet other embodiments, given the flexible nature of the device, it is possible to twist two separate extensions around each other, thus forming a single extension that comprises a twisted (helical) portion of a device, which can have two separate triggers to operate the pulling of cords extending in the separate extended, twisted portions. This facilitates further options for a user in certain situations where an additional set of operable distal features, such as a separate set of jaws, may be useful.

A further object of the present invention is to provide a light source associated with the central portion section in connection with elongate gripper tools and the netting structures associated with the thrombectomy catheter devices described herein. A lighting source can also be positioned at the distal end of the device so that a user can more readily see the distal end and facilitate proper positioning of the distal end to perform operations, such as clamping of jaws around a distant object that may be in a darkened environment. LED lighting sources with small, battery powered energy sources are preferred, but one of skill in the art will appreciate, given the guidance provided herein, the vast variety of other lighting arrangements and features that can be employed while still being within the scope of the claimed invention, including fiber opti fibers, including those employed as a guidewire for the articulated device as described herein. A magnifying viewing device (e.g., a distally or proximatally positioned camera) can also be provided to assist the user in viewing the distal end of the device in particular applications, such as when a detailed and sensitive manipulation of a remote object is required and the user requires magnification of the distal end to properly position the device to perform desired functions.

Conventional therapies to treat stroke include thrombolytic therapy and catheter directed thrombectomy (CDT). Drawbacks of thrombolytic therapy include hemorrhagic risk. Conventional CDT systems often employ an introducer sheath or catheter to the target site, with such larger introducer sheaths increasing the risk of trauma to the patient, and being harder to navigate through the vessels. Conventional catheter devices use a shaft comprising an outer tube connected to the sheath and an inner shaft such that the proximal movement of the sheath is accomplished by imposing an endwise tension on the outer tube, with the inner shaft carrying an endwise compression stress, e.g. see WO 2003/003944, WO 2003/002020, and WO 2004/062458. One disadvantage is that in use, such devices require the medical practitioner to maintain the device in an unchanged axial disposition relative to the site in the body of the patient, while pulling back on the outer tube of the shaft to release the expandable portion of the device. This pulling back of the outer tube requires relative movement of the outer tube in the bodily lumen (or guide catheter) in which it has been advanced to the site of the thrombus. Any friction or resistance to axial movement of the outer tube in the lumen in which it is located hinders the objective of maintaining the device in a precise disposition.

BRIEF DESCRIPTION OF THE DRAWINGS

Other advantages of the present invention will be readily appreciated as the same becomes better understood by reference to the following detailed description when considered with the accompanying drawings, wherein.

WRITTEN DESCRIPTION OF CERTAIN PREFERRED EMBODIMENTS

Figure 1:
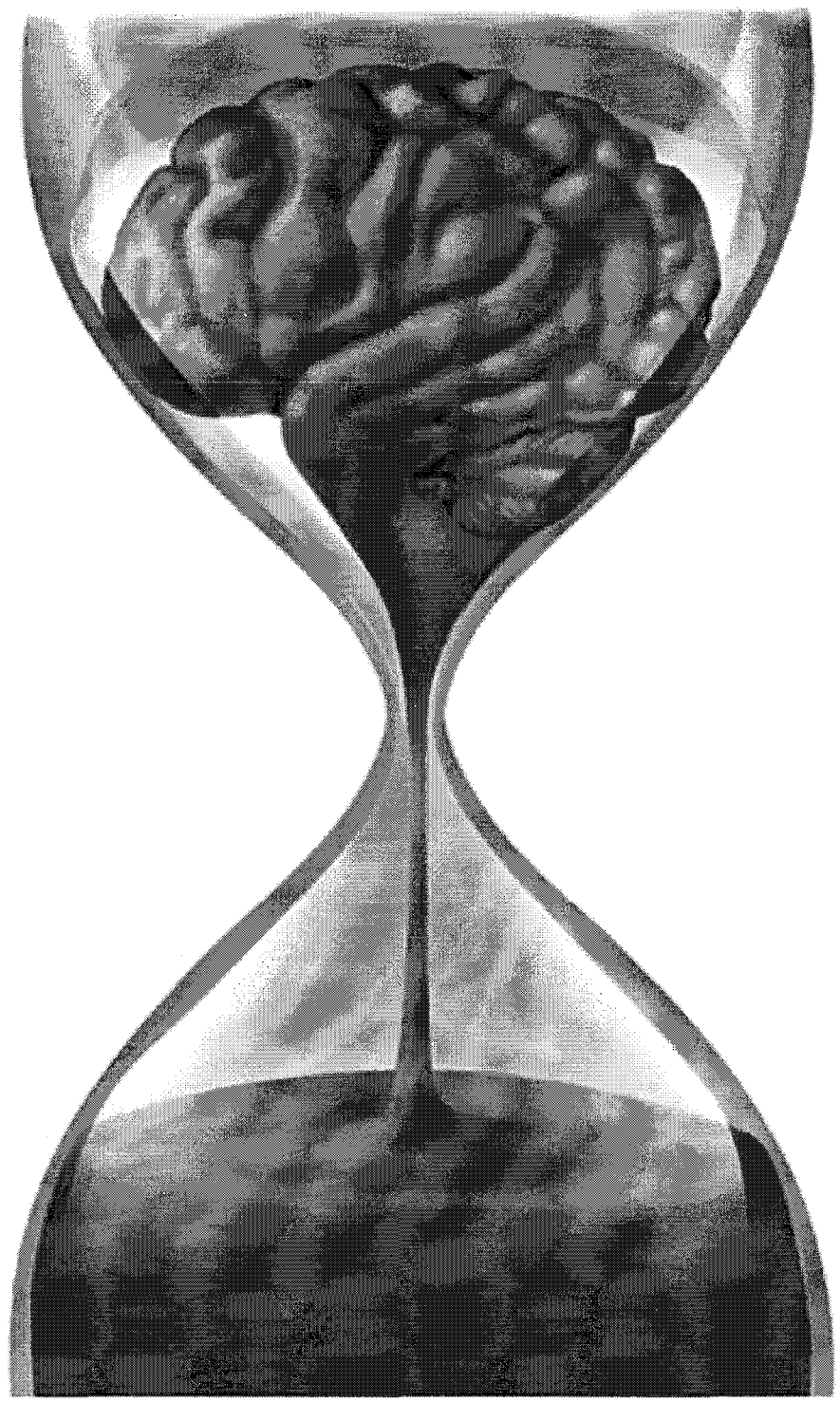
FIG. 1 illustrates the key emphasis in the treatment of stroke victims: "Time is Brain."

It will be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention. For the following description, the actuatable tool head assembly is described as a gripper having a jaw assembly 11. It is understood, however, that any type of actuatable tool head assembly may be used.

As disclosed in the figures, various embodiments of the present invention generally comprise a hand-held gripping device having a jaw portion (indicated generally at 10) comprising a pair of jaws 11a, 11b and a handle portion (indicated generally at 40) spaced apart by a selectively extendible central portion (indicated generally at 70). The handle portion 40 comprises a manually-actuatable trigger 41 operatively connected to the jaws of the jaw portion by a pull member. Actuation of the trigger 41 is operative to move the pull member to thereby selectively position the pair of jaws 11a, 11b between fully clamped and fully opened positions thereof. It will be understood that the jaw construction and the handle portion construction is intended as exemplary only, and that those of skill in the art will appreciate how to adapt such portions as desired, consistent with facilitating operation of the bendable column gripping device as hereinafter described.

A pull member is interconnected with the jaw and handle portions such that manual actuation of the trigger 41 effects movement of the jaws 11a, 11b. In certain embodiments, the user-actuatable release trigger 41 of the present invention comprises a release button 42 disposed on the trigger 41 of the handle portion 40. In the event that the distance between the jaw portion 11 and the handle portion 40 is not appropriate in light of the task contemplated by the user, the user may adjust the length of the central portion by first unscrewing a collet assembly 80 to thus permit telescoping movement of first and second tubular members. The user next actuates the release trigger, either by depressing the release button or turning the collar (depending on the form of the invention), which actions cause the second coupling to move from the engaged to the disengaged position. At this point, the pull member may be lengthened or shortened concurrently with telescoping movement of the first and second tubular members. Thus, while depressing the release trigger 42, the user grasps the second tubular member and changes the distance between the handle portion and the gripping portion as desired. After the desired length is obtained, the user releases release trigger and tightens the collet assembly to thereby fix the lengths of each of the central portion and the pull member.

Selective positioning of the first and second tubular members may be effected by rotational movement of one of the first or second tubular members of the central portion.

In certain embodiments, the gripping device of this embodiment comprises a selectively extendible central portion 70 including a first tubular member 71 slidingly telescopingly received within a second, larger-diameter tubular member 73. In order to fix the relative positions of the first 71 and second 73 tubular members, there is provided a collet assembly 80.

A locking mechanism may be provided to fix the pivotal position of the trigger 41, and thereby fix the relative positions of the jaws 11 between the fully open and fully closed positions thereof.

In operation, from the position wherein the jaws 11 are fully opened, a user manually depresses trigger 41 to retract the pull rod/cord 50 and thereby move the jaws 11 toward each other.

To understand and appreciate the varied and numerous applications of the present invention in the context of tools that do not employ the gripping jaw device used as an illustrative example herein, the inventors incorporate by reference herein, in their entireties, the following patents to provide the detailed embodiments that, with the features here described, facilitate far easier access to previously difficult to reach areas so that the various functional assemblies at the remote end of a tool can be used effectively: Hsu, U.S. Pat. Nos. 6,513,844, 6,520,556, and 6,739,637, 4,669,769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 7,665,782 to Buzby et al.; 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957 to Traber; U.S. Pat. Nos. 4,709,839; 3,527,492 to Hollis; U.S. Pat. No. 4,613,179 to van Zelm; U.S. Pat. No. 4,669,769 to Polder; U.S. Pat. No. 6,257,634 to Wei; U.S. Pat. No. 7,004,520 to Khubani; U.S. Pat. No. 6,513,844 to Hsu; U.S. Pat. No. 6,571,479 to Wu; and U.S. Pat. No. 6,848,731 to Khubani; U.S. Pat. No. 4,033,618 to Lamb; U.S. Pat. No. 5,823,592 to Kalidindi; U.S. Pat. No. 4,483,562 to Schoolman; U.S. Pat. No. 5,647,622 to Schectman; U.S. Pat. No. 1,519,938 to Smith; U.S. Pat. No. 2,947,564 to Winther; U.S. Pat. Publication No. 2003/0236549 to Bonadio, et al; U.S. Pat. No. 5,776,196 to Griffiths; U.S. Pat. No. 7,934,756 to Kroeze, U.S. Pat. No. 4,253,697 to Acosta and 2016/0030596 to Kheir et al.

It will be appreciated from the above disclosure that the present invention improves upon the prior art by providing a bendable gripping device that is robust yet simple in design, and that allows easy adjustment of the direction of the jaws 11 to reach around tight corners or other places where a straight columned device would simply not function to retrieve desired objects remote from the user.

In one embodiment, a hand held gripping device is provided that has a jaw portion comprising a pair of jaws 11 that are movable relative to each other between fully clamped and fully open positions. A handle portion 40 is spaced apart from the jaw portion 11 by a selectively extendable portion, the handle portion having a manually actuable trigger connected to the jaw portion. An extendable pole member, preferably running longitudinally through a tubular section, operatively connecting the jaw portion 11 to the handle portion 40, is provided. Actuation of the trigger 41 is therefore operative to move the pole member to selectively position the pair of jaws 11 between fully clamped and fully opened positions. Between the jaw portion 11 and the handle portion 40 is therefore a central portion, preferably comprising a hollow, corrugated member 30. Such corrugated member 30 preferably has alternating ridges and grooves such that the central portion of the device is able to bend in order to attain predetermined shapes. In particular embodiments, at least one cord is connected between the handle portion and the jaw portion 11, such that the cord extends through the central portion of the device.

Figure 2A:
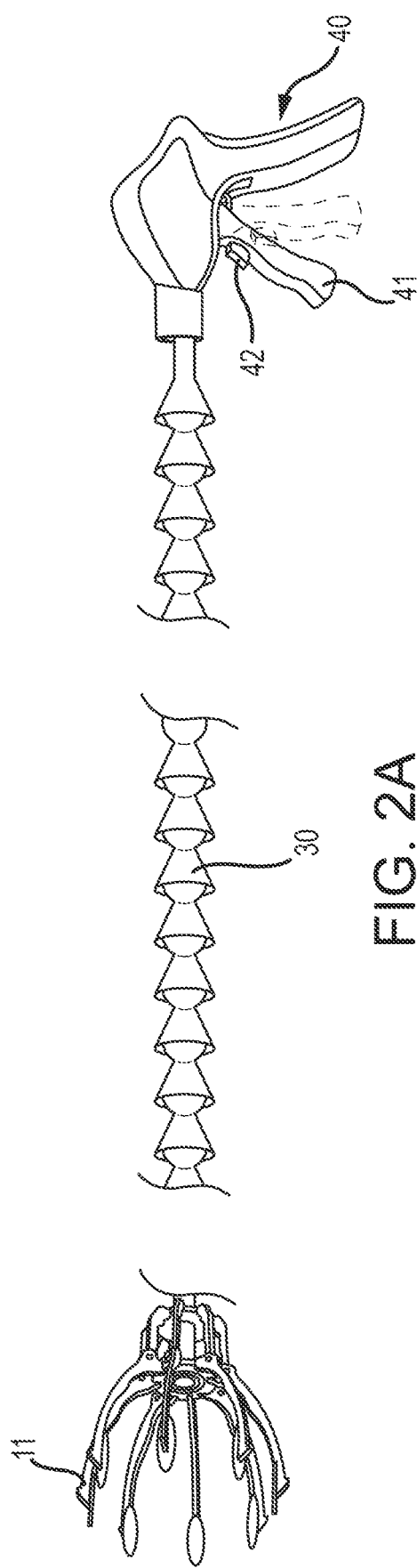
FIG. 2A is a perspective view of a surgical device having differently configured grasping structures that are adapted to be reversibly opened/closed via operation of the handle trigger.
Figure 2B:
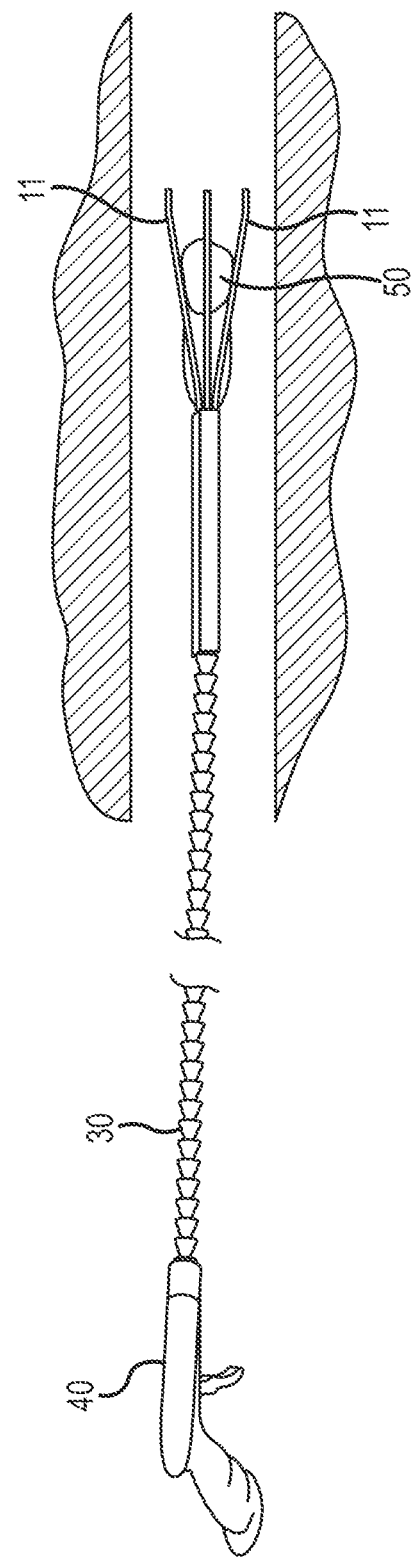
FIG. 2B shows one embodiment where the flexible grasping tool is employed to access an object in a patient's cerebral artery (not to scale).
Figure 7:
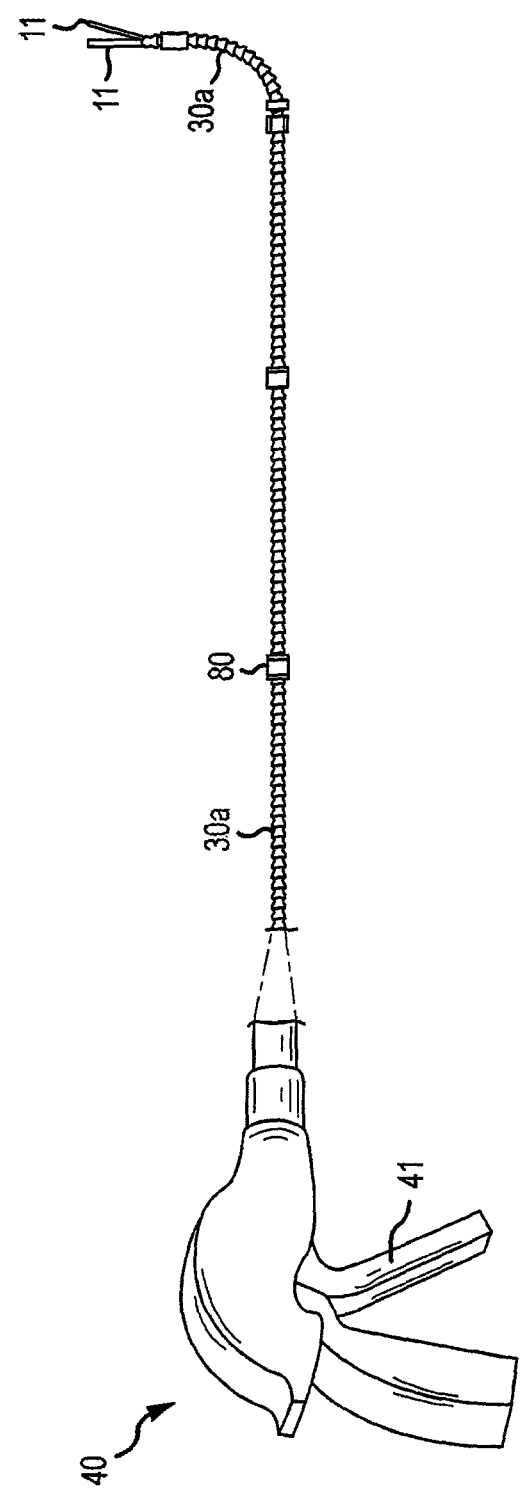
FIG. 7 shows an embodiment where the flexible grasping tool has adjustable locking collars along its extent.
Figure 8:
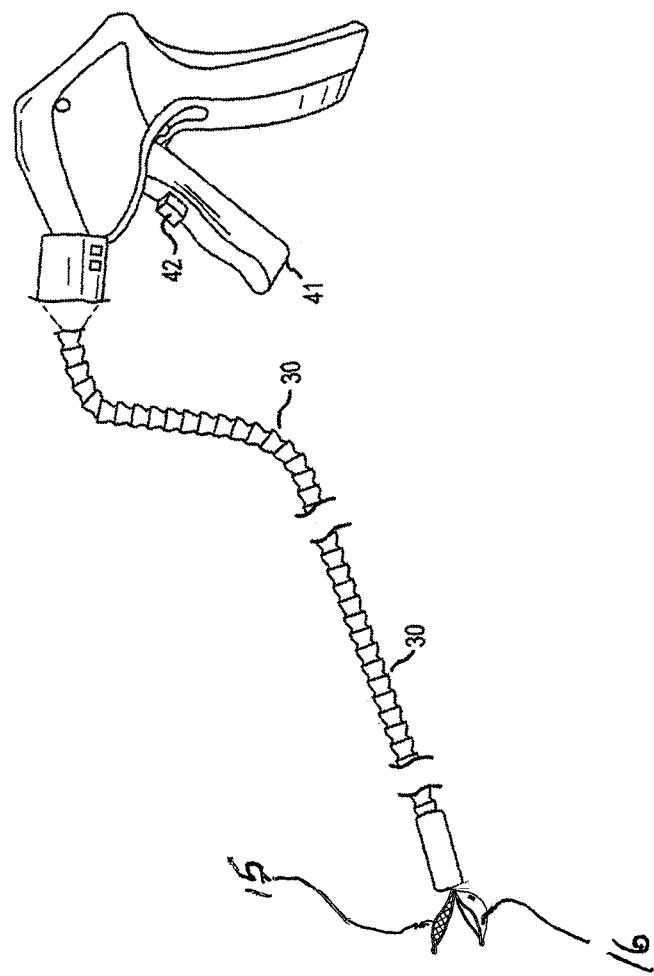
FIG. 8 shows a perspective view of a variable length flexible grasper having a miniature net assembly at its distal end.
Figure 9:
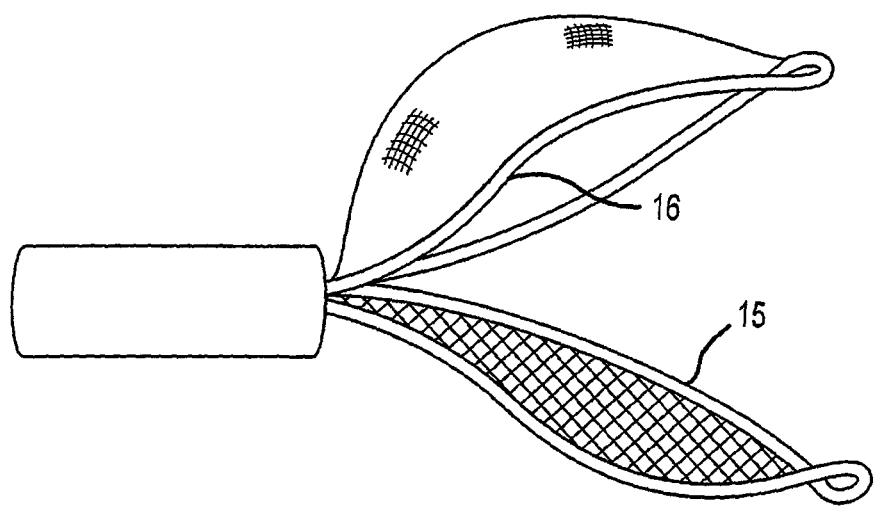
FIG. 9 shows another embodiment illustrating a net assembly with one structure with a loose net and the opposing structure with a taut net.

As illustrated in FIG. 2, in certain embodiments of the present invention, two or more corrugated members 30 are provided at different relative locations along the device, and more specifically along the central portion of the device. In preferred embodiments, at least two thirds of the central portion comprise the corrugated member 30. A locking member 80, preferably a locking collar, may be associated with a central portion. (FIG. 7). The locking member 80 can alternatively be referred to as a coupling member. In a preferred embodiment, the locking member 80 comprises a selectively radially expandable mandrel.

In other embodiments, a user actuable trigger 41 comprises two operable triggers with the operation of a first trigger 41 causing the reversal opening and closing of the jaws 11, whereas the other trigger (not shown) causes the distal end of the device to move such that the distal end bends in relationship to the longitudinal axis of the device. In other embodiments, a selective positioning of a knob (not shown), such knob position near the trigger/handle portion of the device, is provided in order to cause rotational movement of the distal end of the device through manual adjustment of the knob.

In still other embodiments the majority of the portion between the handle portion and the jaw portion comprises corrugated material 30. In such an embodiment, a locking member 80 can be employed, so as to selectively adjust the length of the device in a telescoping relationship, even though the telescoping members themselves are made of a corrugated, bendable material. In other embodiments, however, the locking member 80 can be dispensed with, and the corrugated member 30 can comprise the entirety of the portion between the handle portion 40 and the jaw portion 11 of the device. In such embodiments, it is possible to compress the device in a coiled manner, making transportation and storage of such a device far easier.

An objective is to provide a gripping device including a locking mechanism for locking the gripping jaws, claws, grasping members, 11 etc. in a holding or grasping or gripping position. Thus, in certain embodiments a device is provided that includes a handle body, a hand grip 40 secured to the handle body having a trigger 41 connected to a cord that extends through a flexible corridor 30, preferably one that is corrugated, and more preferably constructed of loc-line elements linked together, at least one gripping jaw or claw 11 movable via manipulation of the trigger 41, and a locking mechanism for locking the jaw or claw 11 into a closed position. The locking mechanism which may be associated with a release trigger 42, may include, for example, a pawl rotatably secured to a hand grip and having a first end for engaging with the handle body, the handle body including a plurality of teeth formed therein with the pawl including teeth for engaging with the teeth of the handle body. One of skill in the art, however, will appreciate the varied other locking devices that can supplant the pawl/teeth design of locking mechanisms that can be employed with the present invention.

In more general embodiments, the present invention is directed to a hand-held reacher for gripping an object and includes a handle portion 40, a jaw portion 10, and a shaft extending between the handle portion and the jaw portion, with such extended portion including at least one section that is flexible 30, preferably corrugated and most preferably constructed of loc-line-type articulated joints that have hollow interiors to facilitate a cord extending through the interior of the flexible corridor formed. At one end of such a device there is at least one jaw/claw portion 11 having at least one of the jaws 11 movable between an open position and a closed position, and the handle portion 40 having a manually-operable trigger 41 for moving the jaws 11 between the open and closed position. An additional locking member operable via a release trigger 42 for releasably locking the jaws in a closed or partially closed position is also a feature of preferred embodiments.

In still other embodiments, the present invention is directed to a hand-held gripping device having a jaw portion 10 that includes a pair of jaws 11 movable relative to each other between fully clamped and fully opened positions. A handle portion 40 is spaced apart from the jaw portion 10 by a selectively extendible central portion, with the handle portion including a first manually-actuatable trigger 41 operatively connected to the jaw portion 10 by a selectively extendible pull member at least substantially disposed within the bendable, preferably corrugated central portion 30. Actuation of the trigger 41 is operative to move the pull member to thereby selectively position the pair of jaws 11 between the fully clamped and fully opened positions. The central portion can be constructed of various materials, including ball-and-socket connectable members of varying lengths, diameters, etc, with such members having a hollow, interior through which a cord or wire can extend through, thus connecting a handle portion 41 to a movable jaw portion 10 of a device. Preferably such a corrugated member 30 has alternating ridges and grooves, which may be covered by an outer sheath of preferably flexible material, such as rubber, fabric or plastic, with the corrugated member 30 preferably being bendable so as to attain a predetermined shape.

In preferred embodiments, the corrugated member 30 is made of loc-line connected elements that have ball and socket connections that permit substantial flexibility of a connected length thereof. A pull member, such as at least one cord, is operatively connected to the handle portion 40 at one end and to the jaw portion 10 at another end of the device. The cord extends through and is preferably entirely encompassed by the central portion. In one embodiment, the corrugated member 30 has a first configuration whereby prior to actuation of the actuation trigger 41, the pair of jaws 11 is in the fully opened position and the corrugated member is bent. A locking member 80 may be operatively associated with the central portion so that two adjacent members of the central portion can be moved with respect to each other in a slidingly telescoping relationship and can then be locked into place. The locking member 80 may be a selectively radially expandable mandrel, radially expanded into engagement with the adjacent members to permit the length of the pull member to be varied. The corrugated member 30 is preferably constructed of plastic and is adapted to be bendable so as to attain a predetermined shape.

In certain embodiments, at least two portions of the central portion column are made of hollow, corrugated members 30 such that a user can preposition each of the portions for a desired bent configuration. The central portion comprises at least 6 inches of the hollow, corrugated member 30 and two or more corrugated members may be provided at different relative locations along the central portion of the device. Preferably, at least two thirds of the central portion comprise the bendable portion that is adapted to be coiled to facilitate transportation and storage, and further includes a locking member operable between a first locking position and a second unlocking position. The actuatable trigger 41 preferably includes a manually operable release trigger 42. The central portion in certain embodiments also includes a bendable portion made of rubber.

In various embodiments, the distal end portions can be substituted with differently configured mechanisms, such as the replacement of a gripper jaw end with different tool elements. Thus, in certain embodiments, with one device having the handle 40, trigger 41 and flexible central portion 30, one can achieve a myriad of different desired operations simply by removing and replacing end tools that have complementary detachable housings associated therewith that interact and reversibly connect to the non-handle end of the tool. For example, and departing from a strictly movable jaw member embodiment, certain embodiments of the present invention are directed to a cupping member that may have flexible, rubber-like memory features to reversibly encompass material (by the moving jaw features) and be either integrally connected or reversibly connected to the distal end of the device.

FIG. 2A shows an embodiment with spring-like claw scoop members associated with an articulated, bendable central portion. Incorporated herein by this reference are the following to illustrate the various ways such members can be provided with the flexible and bendable central portion, workable via the trigger handle as described herein: U.S. Pat. No. 7,281,740 to Fields; U.S. Patent Publication No. US/2009/0200812 to Mambru; U.S. Pat. No. 4,477,111 to Crooks U.S. Pat. No. 6,106,042 to McCloy and U.S. Patent Publication No. 2014/0152031 to Ballacchino.

Figure 3:
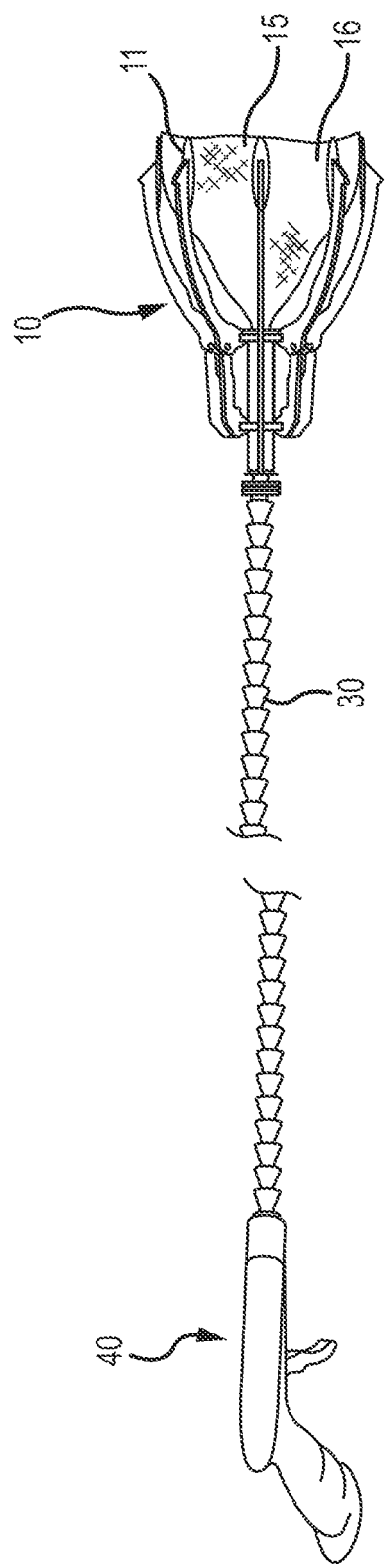
FIG. 3 shows a perspective view of a variable length flexible grasper with a miniature movable jaw assembly and associated bag/net structures.

FIG. 3 discloses another embodiment with multiple-claw scoop members having a bag/net associated therewith, connected to an articulated, bendable central portion and trigger handle. As mentioned above, the employment of such spring-like fingers on the operational end of the tool permits the triggered handle to manipulate the materials to be grasped, and provides for a significant variety of weights, materials, constructions, etc. to be employed.

Various net assemblies, ranging in shape, design, materials, dimensions, and orientation with respect to the central column, etc. can be employed. The hand-held netting tool is preferably adapted to permit reversibly disassociable net attachments such that different types, designs, sizes, mesh patterns, geometries, etc. can be accommodated by a user's selection of desired nets for particular uses. The various ways the net pairs can be reversibly attached will be readily appreciated by those skilled in the art, but one preferred way is to fashion the distal end of the device with a fitted connector that can be pulled outward via a spring attachment associated with the cord extending through the device. A mating hook structure may be employed to attach associated net pairs to the bendable tool at such distal end. Different kinds and sizes of net heads may be attached to allow for a wide range of different configurations. Indeed, in some embodiments, only one net is employed on one side, with the other clamping/closure member being a more rigid net/mesh materials (similar to a tennis racket surface). Thus, in one embodiment the tool comprises a pair of net assemblies where one of the pair is a rectangular shaped wire structure with a loose net associated therewith, and the opposing paired structure is a rectangular shaped wire structure with a taut net associated therewith.

Various embodiments of the present invention relate to a small version of the device as described herein, such a device finding use in a surgical dental or orthodontic environment and other places and situations where very small dimensions are required to fit through spaces, such as lumens, vascular spaces, internal body cavities, etc. Thus, in certain embodiments, the selectively bendable remote gripping tool has relatively small dimensions so it can be easily inserted into the body through known guiding catheters. Various instruments are known in the art for removing various objects/foreign articles 50 from the body, such as instruments used for the removal of objects such as kidney stones, gallstones, blood clots, thrombus clots, occlusions, calcinated plaques, urinary stones or stones of the bile duct; for removing foreign articles from the vascular system of a patient or from a body duct or orifice, such as the ureter or ureteral orifice junction, nasal passages, etc., such foreign articles 50 including vena cava filters, parts of medical devices, such as catheters, guidewires, cardiac leads, etc., which may break and become detached during medical procedures. Most of such instruments employ a flexible catheter formed as a tubular sheath adapted to penetrate body passages to reach the location from where the object is to be evacuated, typically employing flexible wires to snare or capture targeted objects.

Incorporated herein by this reference in their entireties are the following for details as to the dimensions and materials that may be employed for certain elements and aspects of the present described embodiments: U.S. Pat. Nos. 5,658,296; 6,168,603; and 6,491,698 to Bates et al.; U.S. Pat. No. 5,300,086 to Gory et al.; 5,944,728 to Bates; U.S. Pat. No. 6,331,183 to Suon; and U.S. Pat. No. 6,506,209 to Teruo; U.S. Pat. No. 6,679,893 to Tran; U.S. Pat. No. 8,469,970 to Diamant; 20140276920 to Hendrick; 20140155908 to Rosenbluth; 20130317516 to Teague; 20140121672 to Folk; 20190046218 to Garrison, et. al., and 20100204711 to Kear.

In certain embodiments of the present invention the movable jaws are operable via the trigger on the handle end of the device. In some embodiments, such jaws are preferably constructed to collapse and retract inside an elongated sheath. In the protracted position, the jaws are open so as to grasp the object. The trigger may be operated to grasp an object and subsequent removal of the central portion with its corrugated flexible extent, enables the whole device to be removed from the body organ together with the object immobilized within the jaws/net. In certain embodiments, the reversibly movable opposing grasping structures 11, e.g., jaws, fingers, nets (15, 16), etc. are guided through the body to the site of an object, such as a kidney stone, and is used to grasp and remove the stone, e.g., under the guidance of an endoscope.

Preferably the jaws comprise spring-like fingers 11 with sufficient rigidity to reliably hold a foreign body 50. In other embodiments, the distal end of the device comprises a pair of nets 15, 16 that are movable between open and closed positions such that a foreign body can be entrapped within the nets upon movement of the trigger to move the nets into the closed position. One will appreciate that in certain embodiments, the surgical/dental device described herein is essentially a mere smaller version of the larger device described herein that is able to grasp larger objects.

Figure 4:
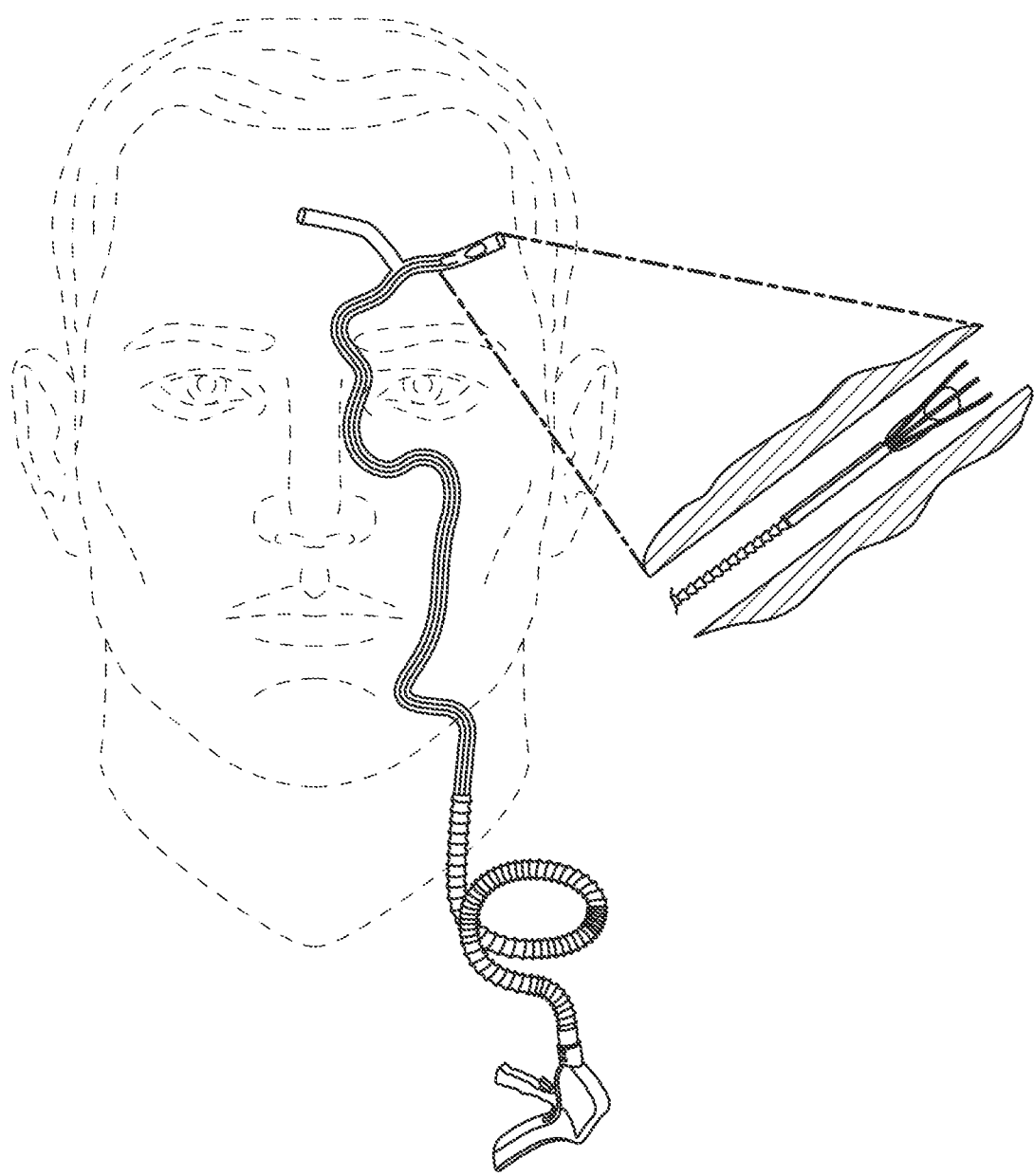
FIG. 4 shows an embodiment as employed to access a patient's cerebral artery.

As illustrated in FIG. 4, a method that can be performed using the present selectively bendable tool is to provide access to a site within the interior portions of a person's anatomy, such as in the femoral artery or other vascular or other peripheral vessels, such as a brachial artery. A guide catheter is advanced and the bendable tool of the present invention is advanced through an inner lumen of such guide catheter until the distal end is positioned adjacent to an object, such as a thromboembolism 50, located in the middle cerebral artery. The physician can then operate the trigger on the handle to cause the grasping assembly so that the jaws 11, net 15, 16 or other grasping elements advance around the thromboembolism 50. In preferred embodiments, there is no need (as in prior art devices) to have the lumen move relative to the grasping jaws/nets so as to constrict the jaw 11 elements around a foreign object, as the operation of the trigger 41 on the handle 40 acts to pull the cord extending through the hollow corrugated structure 30, and causes the jaws/nets 11, 15, 16 to encompass or otherwise grasp the foreign object 50 without the need to have such jaws/nets 11, 15, 16 be in sliding/collapsible contact with a catheter lumen to achieve opening and closing of the gripping elements. It is believed that the present invention, in comparison with prior art devices, therefore provides for a grasping procedure that is less prone to having grasping elements get stuck at a lumens/interface, and that the present invention provides a much more dependable and efficient manner by which foreign objects can be accessed and grasped, with the physician controlling the movement of the jaws/nets 11, 15, 16 without having to worry about the lumen/grasping element frictional movements involved with numerous prior art devices. In other words, unlike prior art systems, such as described by Tran in U.S. Pat. No. 6,679,893, by employing the present invention there is no need to advance a delivery catheter distally to press against proximal arm sections so as to force distal arm sections to rotate radially inwardly to a partially contracted configuration so that object engaging members may engage an object, such as a thromboembolism. Instead, using the present invention, a surgeon is able to operate the trigger hand-held handle to achieve grasping and control of an object.

In yet further embodiments of the present invention, various other features may be included, such as the employment of magnets, cutting elements, ligating elements, etc. Detailed support for how such features can be implemented will be clear to one of skill in the art as guided by the present application, as well as the patent references incorporated herein. For example, magnets may be positioned on the distal end of the device, and the jaws/nets may be supplanted with or added to sharp cutting implements 52 to one or both of the jaws such that a severing operation can be performed. The sharpened cutting jaws 52 can alternatively be operated by a separate handle trigger—or simply provided in a fashion such that the cutting blade can be reversibly retracted by a user (either remotely via a handle trigger operation—or manually, prior to the extension of the device.) Similarly, suction cups can be positioned and affixed to the distal end of the device, whether on the jaws themselves or associated surfaces of the distal end, such that additional securement of remote objects is facilitated. Given the flexible nature of the device, it is possible to twist two separate extensions around each other, thus forming a single extension that comprises a twisted (helical) portion of a device, which can have two separate triggers to operate the pulling of cords extending in the separate extended, twisted portions. This facilitates further options for a user in certain situations where an additional set of operable distal features, such as a separate set of jaws, may be useful. A lighting source can also be positioned at the distal end of the device so that a user can more readily see the distal end and facilitate proper positioning of the distal end to perform operations, such as clamping of jaws around a distant object that may be in a darkened environment. LED lighting sources with small, battery powered energy sources are preferred, but one of skill in the art will appreciate, given the guidance provided herein, the vast variety of other lighting arrangements and features that can be employed while still being within the scope of the claimed invention. A magnifying viewing device (e.g., a distally positioned camera) can also be provided to assist the user in viewing the distal end of the device in particular applications, such as when a detailed and sensitive manipulation of a remote object is required and the user requires magnification of the distal end to properly position the device to perform desired functions.

Figure 5:
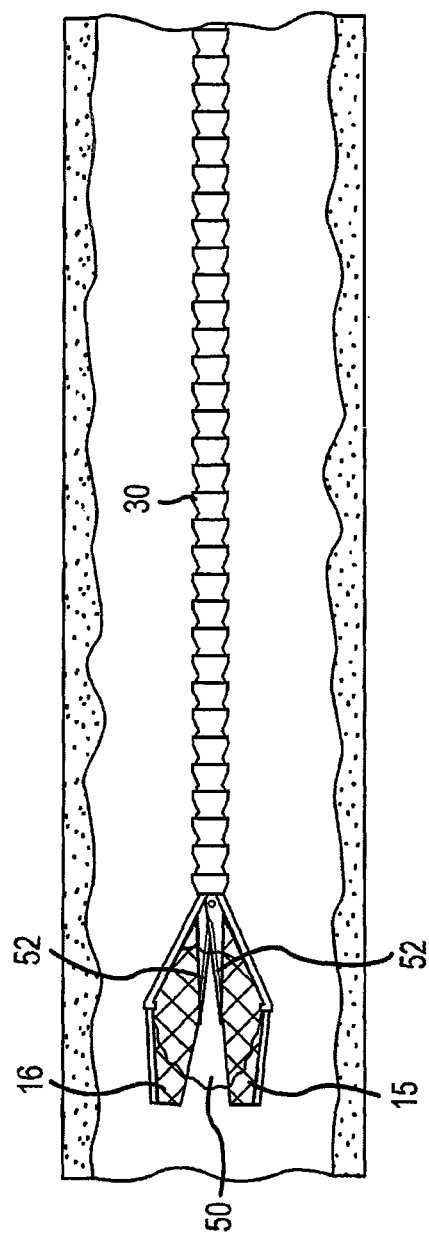
FIG. 5 shows an embodiment where opposing nets and cutting jaws are shown to facilitate reduction in the size of a blood clot, stone or foreign object prior to or after grasping the object within the opposing collapsible nets.

FIG. 5 shows an embodiment where opposing nets 15, 16 and cutting jaws 52 are shown to facilitate reduction in the size of an object 50, such as a blood clot, stone or foreign object, prior to or after grasping the object within the opposing collapsible nets 15, 16. Thus, in certain embodiments, a physician can operate the trigger 41 on the handle 40 to cause the grasping assembly 10 to cause the jaws 11, net 15, 16 or other grasping elements advance around a thromboembolism, foreign object or stone 50, and once secured in the grasp of the tool, the object 50 can then be cut into pieces via one or more cutting operations via the reversible closure of the cutting blades 52, also operable via a cord extending through the corrugated central portion 30 and operably connected to a trigger 4 workable by the surgeon. In such a manner, the prior difficulties and problems experienced with attempting to grasp and pull or advance a foreign object (e.g. a stone, thrombus, etc.) through a delicate tissue lumen, e.g., due to the girth and size of such objects, is addressed by either cutting such object 50 prior to grasping the same, or more preferably, by grasping the object 50, either via the jaws 11, spring-like fingers 11 or nets 15, 16 as disclosed herein, and then closing the sharp cutting implements 52 associated with one or more of the jaws 11, fingers 11 or nets 15, 16, such that a severing operation can be performed. The pieces of the object 50 are thus entrapped in the jaws 11 or nets 15, 16 and can be safely removed from the lumen without the threat of damage to the lumen tissue upon removal.

Thus, various embodiments are directed to a selectively bendable remote gripping tool for entrapping an object located in an interior portion of a person's anatomy to achieve its extraction therefrom, the tool comprising a jaw portion 10 having a pair of net assemblies 15, 16 movable relative to each other between fully clamped and fully opened positions thereof; a handle portion 40 spaced apart from the jaw portion 10 by a selectively extendible central portion, the handle portion 40 comprising a first manually-actuatable trigger 41 operatively connected to the jaw portion 10 by a selectively extendible pull member at least substantially disposed within the central portion 70. Actuation of the trigger 41 is operative to move the pull member to thereby selectively position the pair of net assemblies 15, 16 between the fully clamped and fully opened positions. The central portion 70 preferably comprises at least two separate portions that include hollow, corrugated members 30 that have alternating ridges and grooves, with the central portion 7—being bendable so as to position the tool into a desired bent configuration. A pull member comprising at least one cord operatively connects the handle portion 40 to the jaw portion 10, with the at least one cord extending through the central portion. Miniature versions of the tool are adapted and configured for withdrawing thromboembolic material and other foreign objects 50 from body lumens and cavities, employing a pair of jaws 11, nets 15, 16, or a combination thereof. Thus, in certain embodiments the invention is directed to a method and apparatus for managing polyps by which an elongated corrugated flexible member is positionable within a working channel of an endoscopic device, with a selectively bendable central column that at its distal end has opposing nets 15, 16 that are movable between open and closed positions via a handle 40 having a trigger 41 that operates the nets 15, 16, thus allowing a physician to, for example, grasp an object 50, such as portion of a foreign body, a polyp, a clot, a stone, etc. in a fashion that retains the object for removal with the corrugated flexible member 30.

Figure 6:
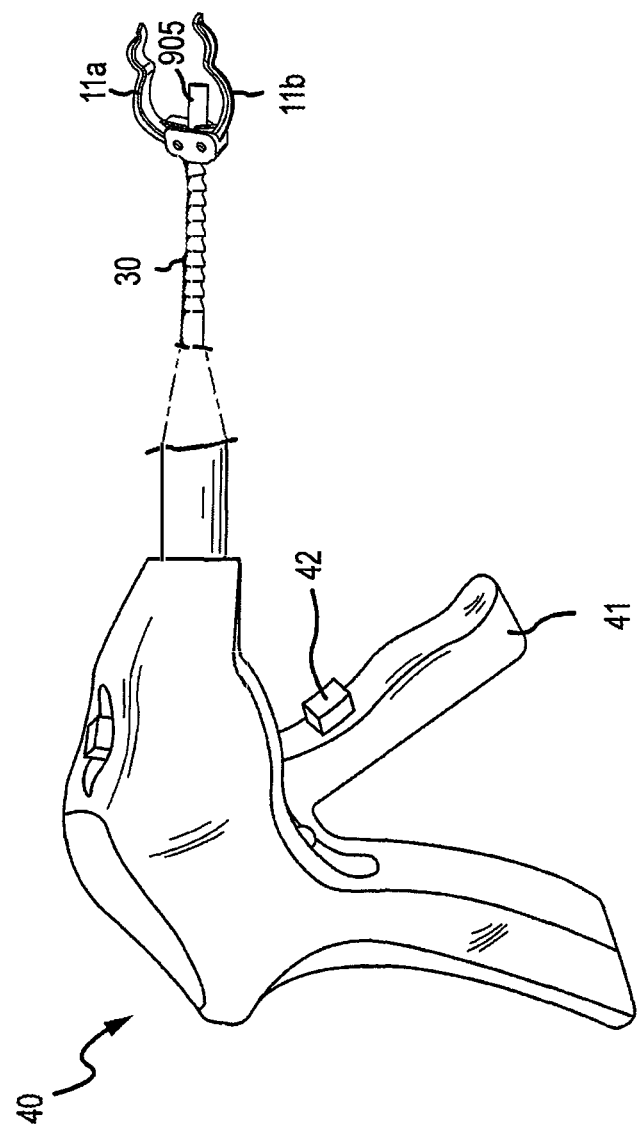
FIG. 6 is a perspective view of another embodiment showing the engagement elements (jaws) and a lighting element.

As shown in FIG. 6, other embodiments may include one or more other features, such as a suction cup, a lighting element 905, a magnifying viewing device, and a camera may be affixed to a distal portion of the device, near to, for example, the gripping portion 10 of the device. For example, FIG. 6 shows a lighting element 905 in association with the engagement elements (jaws 11a, 11b). Also incorporated herein by this reference is US patent publication no. 2013/0096457 to Qui, et al. with respect to various embodiments of lighting elements that may be employed.

Thromboembolism is a leading cause of morbidity and mortality globally. Survival after VTE (venous thromboembolism including deep venous thrombosis and pulmonary embolism) is often not possible, and even survival entails significant pain and disability. The risk of death after a pulmonary embolism (PE) is 18-fold higher than after a deep vein thrombosis (DVT). VTE also poses a significant burden globally in terms of disability-adjusted life years (DALYs) lost in low-, middle-, and high-income countries. Approximately one in four deaths worldwide is attributed to arterial thromboembolic conditions. These arterial thromboses primarily include myocardial infarction, ischemic strokes, and limb ischemia, whereas deep vein thrombosis and pulmonary embolism comprise the bulk of venous thrombosis.

With respect to the causes of thrombosis, one's own blood vessel wall provides adhesion receptors that enable recruitment of leukocytes and platelets to sites of vascular injury and dysfunction. Upon injury, endothelium expresses tissue factor and exposes vascular smooth muscle tissue factor that is constitutively present. Additionally, vascular endothelial cells are constantly subjected to mechanical shear stress imposed by blood flow. Fluid shear stress itself through oscillatory and turbulent flow regulates vascular biology and pathology by ordering changes in protein expression via induction of vascular transcription factors. In certain embodiments focused on the treatment of arterial (vs. venous) thrombosis, oxygen is provided to the distal tip region of the device such that oxygen starved tissue has a better chance of surviving until blood flow is restored.

Certain embodiments comprise features provided on the distal portion of the device to provide oxygen (or other lifesaving materials) so that starved tissues can hope to survive until blood flow to such tissue is restored. In certain embodiments, this entails the encapsulation of an oxygen containing substance to assist cells survive until blood flow returns with oxygenated blood.

One severe drawback to current acute stroke interventions is the amount of time required to restore blood perfusion to the brain, which can be broken down to time required to access to the blocked cerebral artery, and time required to restore flow through the occlusion. Restoration of flow, either through thrombolytic therapy, mechanical thrombectomy, or other means, often takes hours during which time brain tissue is deprived of adequate oxygen. During this period, there is a risk of permanent injury to the brain tissue. Means to shorten the procedure time, and/or to provide oxygen to the brain tissue during the procedure, would reduce this risk.

Trauma is the leading cause of mortality and years of life lost in the United States. Trauma victims require emergent evaluation and definitive care of their injuries in the trauma room. Every 3 min delay in management can increase the mortality of trauma patient by 1%. Over the recent years, latest advances in technology and their successful integration in healthcare sector led to the development of state-of-the-art diagnostic and treatment modalities. It has improved the organizational efficiency of hospitals and the standard of care for time-sensitive ailments especially trauma.

About 85 percent of strokes are ischemic, meaning the stroke is caused by a blood clot that blocks blood flow to an area of the brain. Starved of blood and oxygen, brain cells begin dying. After an ischemic stroke strikes, a core of brain tissue begins to die. Around this core is a penumbra of cells that continue to receive blood from surrounding arteries in a process called collateral circulation. Collateral circulation can keep cells in the penumbra alive for a time before they too begin to die. Good circulation slows down the rate at which the cells die.

Ischemic stroke occurs when a blockage in an artery leading to the brain causes a lack of supply of oxygen and nutrients to the brain tissue. The brain relies on its arteries to supply oxygenated blood from the heart and lungs. The blood returning from the brain carries carbon dioxide and cellular waste. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient.

The term "myocardial infarction", as used herein, refers to death of cells of an area of heart muscle as a result of oxygen deprivation, which in turn is caused by obstruction of the blood supply; commonly referred to as a "heart attack". The most common cause is thrombosis of an atherosclerotic coronary artery or a spasm. Less common causes included coronary artery abnormalities and vasculitis (inflammation of blood vessels).

Figure 10:
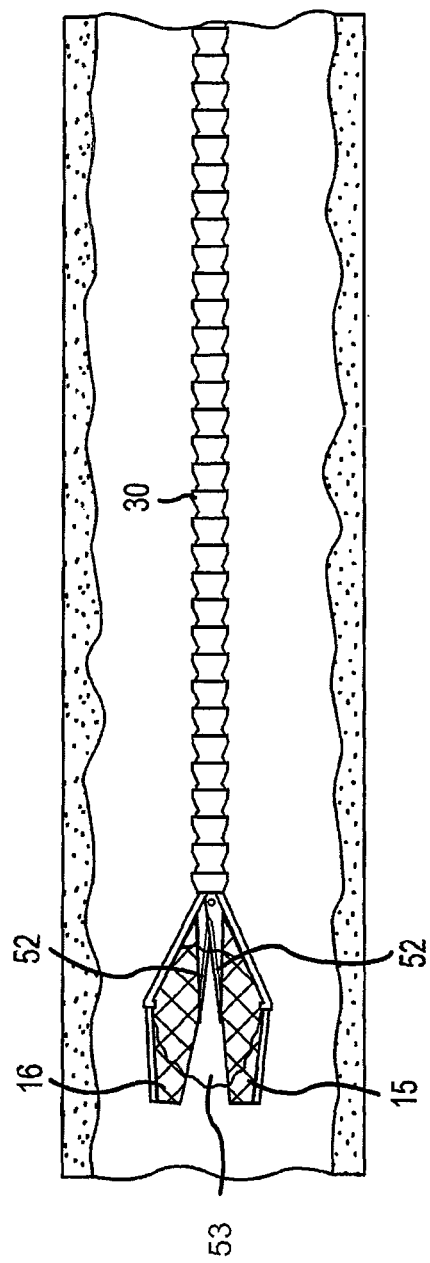
FIG. 10 shows another embodiment illustrating a net assembly with a capsule of oxygen containing material associated with the net assemblies, positioned such that the sharp cutting implements can fracture the capsule to release the oxygen contained therein.

In various embodiments of the present invention, there is described methods and devices that enable safe and rapid access to the cerebral arteries to treat acute ischemic stroke, and to provide tissue-saving oxygen sources to tissues that are being deprived of oxygen due to a thrombus. The methods and devices include the devices described herein, e.g. the net assemblies that capture and cut up the thrombus, and to otherwise remove the occlusion. The disclosed methods and devices also include methods and devices to protect the cerebral penumbra during the procedure to minimize injury to brain, including provision of oxygen to tissues in need thereof, either via the fracturing of an encapsulated enclosure containing oxygen containing material, which may in some embodiments comprise bacteria that may provide a source of oxygen, various fluids that are able to emit oxygen in a manner to assist the tissue starved from oxygen to survive longer than they would otherwise without such source of oxygen, etc. FIG. 10 shows another embodiment illustrating a net assembly 15, 16 with a capsule of oxygen 53 containing material associated with the net assemblies 15, 16, positioned such that the sharp cutting implements 52 can fracture the capsule 53 to release the oxygen contained therein.

In one aspect, there is disclosed a system for treating an occlusion in a cerebral artery of a patient, comprising: a selectively bendable remote gripping tool comprising: a jaw portion comprising at least one of: (ij:\6773) a pair of net assemblies 15, 16 movable relative to each other between closed and opened positions thereof; and (ii) a pair of sharp cutting implements associated with said jaw portion, a handle portion spaced apart from the jaw portion by a central portion, the handle portion comprising a first actuatable trigger operatively connected to the jaw portion by a pull member at least substantially disposed within the central portion, whereby actuation of the trigger is operative to move the pull member to thereby selectively position the pair of jaw portion between the closed and opened positions thereof; wherein the central portion comprises adjacent members of linked ball and socket jointed elements forming a plurality of interconnected connectors, thereby permitting pivoting movement with respect to said interconnected connectors; and the pull member comprising at least one cord operatively connecting the handle portion to the jaw portion. At least one magnet positioned on a distal end of the tool (and which may be part of the net assemblies 15, 16 frames, etc.) and wherein said pair of sharp cutting implements 52 is positioned within an interior volume defined by the pair of net assemblies 15, 16 to perform a severing operation when the net assemblies 15, 16 are in said closed position. A capsule of oxygen containing material 53 is associated with the distal end of the tool, preferably connected to the net assemblies 15, 16, and even more preferably within the net assemblies 15, 16, when closed and positioned such that the sharp cutting implement 52 can fracture, cut or otherwise act to release the oxygen contained within the enclosure 53 such that oxygen can be delivered to the local tissue adjacent the distal end of the device. In such a manner, as the occlusion is being removed, tissue saving supplies of oxygen can be administered in discreet volumes and directly to the tissues starved of oxygen, thus permitting far better outcomes for patients who have suffered a stroke. Alternatively or in addition to the provision of oxygen via the encapsulated structures 53 as described herein, a source of oxygen can be provide that can travel through the interior of the device, through the central hole/cavity tunnel formed via the connected loc-line units 30 of the device, such that oxygen fluid or gas can be conveyed along the extent of the device to arrive at the point where the occlusion is being removed, thus providing additional oxygen to starved tissue.

While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention. It is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

What is claimed is:

1. An apparatus for performing a minimally-invasive procedure, the apparatus comprising:
    a shaft having a distal end, a proximal end and a central portion extending between the distal end and the proximal end,
    wherein the shaft comprises a flexible portion that extends distally from a handle portion at the proximal end of the shaft, said shaft having its distal end, an actuatable tool head assembly comprising a sharp cutting implement;
    wherein the handle portion comprises a first actuatable trigger operatively connected to a pull member at least substantially disposed within the central portion;
    whereby actuation of the trigger is operative to move the pull member to thereby selectively position the actuatable tool head assembly, said pull member comprising at least one cord operatively connected to the handle portion and that extends through a center of the central portion; wherein said sharp cutting implement comprises a pair of functional assemblies at a remote end of the apparatus movable relative to each other between fully closed and fully opened positions.

2. The apparatus as set forth in claim 1, wherein the shaft comprises first and second tubular members, at least one being rotatable to selectively position one of the first and second tubular members.

3. The apparatus as set forth in claim 1, wherein the shaft comprises ball-and-socket members.

4. The apparatus as set forth in claim 1, wherein the central portion comprises adjacent members of linked ball and socket jointed elements forming a plurality of interconnected connectors.

5. The apparatus as set forth in claim 1, wherein the flexible portion comprises plastic components.

6. The apparatus as set forth in claim 1, further comprising a lighting source positioned at the distal end of the shaft.

7. The apparatus as set forth in claim 1, further comprising a magnifying viewing device at the distal end of the shaft.

8. The apparatus as set forth in claim 1, further comprising a camera positioned at the distal end of the shaft.

9. The apparatus as set forth in claim 1, further comprising a knob positioned near the handle portion adapted to cause movement of the actuatable tool head assembly by manual adjustment of the knob.

* * * * *